United States Patent
Kussie et al.

(10) Patent No.: US 9,592,331 B2
(45) Date of Patent: Mar. 14, 2017

(54) METHODS AND SYSTEMS FOR TREATING ECLAMPSIA OR PRE-ECLAMPSIA

(75) Inventors: Paul Kussie, New York, NY (US); Woo S. Joo, New York, NY (US)

(73) Assignee: AGGAMIN LLC, New York, NY (US)

( * ) Notice: Subject to any disclaimer, the term of this patent is extended or adjusted under 35 U.S.C. 154(b) by 464 days.

(21) Appl. No.: 13/984,262

(22) PCT Filed: Feb. 7, 2012

(86) PCT No.: PCT/US2012/024198
§ 371 (c)(1),
(2), (4) Date: Nov. 15, 2013

(87) PCT Pub. No.: WO2012/109282
PCT Pub. Date: Aug. 16, 2012

(65) Prior Publication Data
US 2014/0065150 A1    Mar. 6, 2014

Related U.S. Application Data

(60) Provisional application No. 61/440,169, filed on Feb. 7, 2011.

(51) Int. Cl.
| | |
|---|---|
| A61K 39/395 | (2006.01) |
| C07K 16/18 | (2006.01) |
| C07K 16/28 | (2006.01) |
| A61M 1/34 | (2006.01) |
| C07K 14/71 | (2006.01) |

(52) U.S. Cl.
CPC ............ *A61M 1/34* (2013.01); *A61M 1/3486* (2014.02); *C07K 14/71* (2013.01); *C07K 16/2863* (2013.01); *C07K 2317/24* (2013.01); *C07K 2317/41* (2013.01); *C07K 2317/52* (2013.01); *C07K 2317/71* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,335,362 B2 | 2/2008 | Karumanchi et al. |
| 7,407,659 B2 | 8/2008 | Karumanchi et al. |
| 7,435,419 B2 | 10/2008 | Karumanchi et al. |
| 2003/0086924 A1 | 5/2003 | Sliwkowski |
| 2006/0067937 A1 | 3/2006 | Karumanchi et al. |
| 2007/0065425 A1 | 3/2007 | Behrens et al. |
| 2007/0202113 A1 | 8/2007 | Young et al. |
| 2007/0231333 A1 | 10/2007 | Boghaert et al. |
| 2008/0177045 A1 | 7/2008 | Lee et al. |
| 2009/0169547 A1 | 7/2009 | Sahin et al. |
| 2009/0286271 A1 | 11/2009 | Karumanchi et al. |

FOREIGN PATENT DOCUMENTS

| | | |
|---|---|---|
| WO | 2004/008946 A2 | 1/2004 |
| WO | 2006/076467 A2 | 7/2006 |
| WO | 2010/075475 A1 | 7/2010 |

OTHER PUBLICATIONS

Office Action issued in counterpart Japanese Patent Application No. 2013-552737, dated Feb. 8, 2016.
Barleon, B. et al., "Mapping of the Sites for Ligand Binding and Receptor Dimerization at the Extracellular Domain of the Vascular Endothelial Growth Factor Receptor FLT-1", J. Bio. Chem., (1997), vol. 272:16, pp. 10382-10388.
Davis-Smyth, T. et al., "The second immunoglobulin-like domain of the VEGF tyrosine kinase receptor Flt-1 determines ligand binding and may initiate a signal transduction cascade", EMBO J. (1996), vol. 15:18, pp. 4919-4927.
Kendall, R. et al., "Inhibition of vascular endothelial cell growth factor activity by an endogenously encoded soluble receptor", PNAS (1993), vol. 90, pp. 10705-10709.
Thomas, C. et al., "Itronic polyadenylation signal sequences and alternate splicing generate human soluble Flt1 variants and regulate the abundance of soluble Flt1 in the placenta", FASEB J. (2007), vol. 21(14):3885-3895.
Belgore, F.M. et al., "Measurement of free and complexed soluble vascular endothelial growth factor receptor, Flt-I, in fluid samples: development and application of two new immunoassays", Clinical Science (2000), vol. 100, pp. 567-575.
Zhou, C.C. et al., "Angiotensin II Induces Soluble fms-Like Tyrosine Kinase-1 Release via Calcineurin Signaling Pathway in Pregnancy", Circulation Research (2007), vol. 100, pp. 88-95. Epub Dec. 7, 2006.
Zhou, C.C. et al., "Angiotensin II Induces Soluble fms-Like Tyrosine Kinase-1 Release via Calcineurin Signaling Pathway in Pregnancy", Circulation Research (2007), vol. 100, pp. 88-95. Online Supplemental published Feb. 20, 2007.

*Primary Examiner* — Christine J Saoud
*Assistant Examiner* — Jon M Lockard
(74) *Attorney, Agent, or Firm* — Fox Rothschild LLP

(57) ABSTRACT

Disclosed are methods and apparatuses for treating a pregnancy related hypertensive disorder, such as pre-eclampsia and eclampsia, using ex vivo treatment with an anti-sFlt-1 receptor (sFlt-1) antibody bound to a solid support in order to reduce blood levels of sFlt-1. Further disclosed are the sequences of the heavy chain and light chain CDRs of the anti-sFlt-1 antibodies.

19 Claims, 8 Drawing Sheets

A.

B.

METHODS AND SYSTEMS FOR TREATING ECLAMPSIA OR PRE-ECLAMPSIA

CROSS-REFERENCE TO RELATED APPLICATIONS

This application claims priority to U.S. Application No. 61/440,169, filed Feb. 7, 2011, which is incorporated herein by reference in its entirety.

FIELD OF THE INVENTION

The present invention relates to methods, systems, devices, and apparatuses for treating pregnancy-related hypertensive disorders such as pre-eclampsia and eclampsia.

BACKGROUND OF THE INVENTION

Pre-eclampsia is a syndrome of hypertension, edema, and proteinuria that affects 5 to 10% of pregnancies and results in substantial maternal and fetal morbidity and mortality. Pre-eclampsia accounts for at least 200,000 maternal deaths worldwide per year. The symptoms of pre-eclampsia typically appear after the 20th week of pregnancy and are usually detected by the routine monitoring of blood pressure and urine. However, these monitoring methods are ineffective for diagnosis of pre-eclampsia at an early stage, which could reduce the risk to the subject or developing fetus, if an effective treatment were available.

Symptoms of pre-eclampsia generally include any of the following: (1) a systolic blood pressure (BP)>140 mmHg and a diastolic BP>90 mmHg after 20 weeks gestation, (2) new onset proteinuria (1+ by dipstik on urinanalysis, >300 mg of protein in a 24 hour urine collection, or random urine protein/creatinine ratio>0.3), or (3) resolution of hypertension and proteinuria by 12 weeks postpartum. The symptoms of pre-eclampsia can also include renal dysfunction and glomerular endotheliosis or hypertrophy. Other symptoms of eclampsia may be any of the following symptoms due to pregnancy or the influence of a recent pregnancy: seizures, coma, thrombocytopenia, liver edema, pulmonary edema, or cerebral edema.

Pre-eclampsia can vary in severity from mild to life threatening. A mild form of pre-eclampsia may be treated with bed rest and frequent monitoring. For moderate to severe cases, hospitalization is recommended and blood pressure medications or anticonvulsant medications to prevent seizures are prescribed. If the condition becomes life threatening to the mother or the fetus, the pregnancy is terminated and the fetus is delivered pre-term.

Several factors have been reported to have an association with fetal and placental development and pre-eclampsia. They include vascular endothelial growth factor (VEGF), soluble Flt-1 receptor (sFlt-1), and placental growth factor (PlGF). VEGF is an endothelial cell-specific mitogen, an angiogenic inducer, and a mediator of vascular permeability. VEGF has also been shown to be important for glomerular capillary repair. VEGF is disclosed in U.S. Pat. No. 5,332,671; U.S. Pat. No. 5,240,848; and U.S. Pat. No. 5,194,596; as well as in Charnock-Jones et al., 1993, Biol. Reproduction, 48: 1120-1128. VEGF exists as a glycosylated homodimer and includes at least four different alternatively spliced isoforms. The biological activity of native VEGF includes the promotion of selective growth of vascular endothelial cells or umbilical vein endothelial cells and induction of angiogenesis. VEGF includes several family members or isoforms (e.g., VEGF-A, VEGF-B, VEGF-C, VEGF-D, VEGF-E, VEGF189, VEGF165, or VEGF 121); see Tischer et al., 1991, J. Biol. Chem. 266, 11947-11954; Neufed et al., 1996, Cancer Metastasis 15:153-158; U.S. Pat. No. 6,447,768; U.S. Pat. No. 5,219,739; and U.S. Pat. No. 5,194,596. Also known are mutant forms of VEGF such as the KDR-selective VEGF and Flt-selective VEGF described in Gille et al., 2001, J. Biol. Chem. 276:3222-3230. Modified forms of VEGF are described in LeCouter et al., 2003, Science 299:890-893.

VEGF binds as a homodimer to two homologous membrane-spanning tyrosine kinase receptors, the fms-like tyrosine kinase (Flt-1) and the kinase domain receptor (KDR), which are differentially expressed in endothelial cells obtained from many different tissues. GenBank accession number AF063657 provides the nucleotide and amino acid sequences of human Flt-1. Flt-1, but not KDR, is highly expressed by trophoblast cells which contribute to placental formation. PlGF is a VEGF family member that is also involved in placental development. PlGF is expressed by cytotrophoblasts and syncytiotrophoblasts and is capable of inducing proliferation, migration, and activation of endothelial cells. PlGF binds as a homodimer to the Flt-1 receptor, but not to the KDR receptor. Both PlGF and VEGF contribute to the mitogenic activity and angiogenesis that are critical for the developing placenta.

sFlt-1, which lacks the transmembrane and cytoplasmic domains of the full-length Flt-1 receptor, was identified in the culture medium of human umbilical vein endothelial cells and the in vivo expression of sFlt-1 was subsequently demonstrated in placental tissue. sFlt-1 binds to VEGF with high affinity but does not stimulate mitogenesis of endothelial cells. The elevated levels of sFlt-1 found in the serum samples taken from pregnant women suffering from, or at risk of developing, a pregnancy-related hypertensive disorder (e.g., pre-eclampsia or eclampsia) indicate that sFlt-1 is acting as a "physiologic sink" to bind to and deplete the trophoblast cells and maternal endothelial cells of functional growth factors required for the proper development and angiogenesis of the fetus and/or the placenta.

SUMMARY OF THE INVENTION

The present invention provides a method of treating or preventing a disorder associated with sFlt-1, such as a pregnancy-related hypertensive disorder in a subject comprising providing ex vivo to the subject anti-sFlt-1 antibodies, or sFlt-1 binding fragments thereof, or an sFlt-1 ligand, in an amount sufficient and for a time sufficient to decrease the subject's blood levels of sFlt-1 to treat or prevent the disorder associated with sFlt-1 in the subject.

In certain embodiments, the method comprises removing a volume of the subject's blood, bringing the blood or a component thereof (e.g., plasma) into contact with the anti-sFlt-1 antibodies, or sFlt-1 binding fragments thereof, or sFlt-1 ligands, where the anti-sFlt-1 antibodies, or sFlt-1 binding fragments thereof, or sFlt-1 ligands, are bound to a solid support, to bind sFlt-1 in the subject's blood or component thereof to the anti-sFlt-1 antibodies, or sFlt-1 binding fragments thereof, or sFlt-1 ligands, thereby decreasing the amount of sFlt-1 in the subject's blood or component thereof, and returning the blood or component thereof to the subject.

The invention provides anti-sFlt-1 antibodies and sFlt-1 binding fragments thereof. The antibodies are used in the aforementioned ex vivo methods, and can also be administered to a subject. In certain embodiments, the anti-sFlt-1 antibodies, or sFlt-1 binding fragments thereof, comprise one, two, or three heavy chain CDRs having SEQ ID NO:18, SEQ ID NO:20, and SEQ ID NO:22 and one, two, or three light chain CDRs having SEQ ID NO:24, SEQ ID NO:26, and SEQ ID NO:28. In certain embodiments, the sFlt-1 antibodies comprise one, two, or three heavy chain CDRs having substantially the same sequence as SEQ ID NO:18, SEQ ID NO:20, and SEQ ID NO:22 and one, two, or three light chain CDRs having substantially the same sequence as SEQ ID NO:24, SEQ ID NO:26, and SEQ ID NO:28. In some embodiments, the anti-sFlt-1 antibodies or binding fragments thereof comprise at least one variable region with an amino acid sequence selected from SEQ ID NOS: 30 and 32, or a sequence at least 85% or at least 90% identical thereto.

In certain embodiments, the anti-sFlt-1 antibodies, or sFlt-1 binding fragments thereof, comprise one, two, or three heavy chain CDRs having SEQ ID NO:2, SEQ ID NO:4, and SEQ ID NO:6 and one, two, or three light chain CDRs having SEQ ID NO:8, SEQ ID NO:10, and SEQ ID NO:12. In certain embodiments, the anti-sFlt-1 antibodies comprise one, two, or three heavy chain CDRs having substantially the same sequence as SEQ ID NO:2, SEQ ID NO:4, and SEQ ID NO:6 and one, two, or three light chain CDRs having substantially the same sequence as SEQ ID NO:8, SEQ ID NO:10, and SEQ ID NO:12. In some such embodiments, the anti-sFlt-1 antibodies or binding fragments thereof comprise at least one variable region with an amino acid sequence selected from SEQ ID NOS: 14 and 16, or a sequence at least 85% or at least 90% identical thereto.

In certain embodiments of the invention, the anti-sFlt-1 antibodies do not block ligand binding to sFlt-1. sFlt-1 ligands include PlGF, VEGF, including their isoforms. In certain embodiments, the anti-sFlt-1 antibodies, or sFlt-1 binding fragments thereof, bind to an epitope in sFlt-1 that is not present in Flt-1. In certain embodiments, the anti-sFlt-1 antibodies, or sFlt-1 binding fragments thereof, bind to an epitope that includes amino acids from the carboxy terminus of an sFlt-1 isoform. In certain embodiments, the anti-sFlt-1 antibodies, or sFlt-1 binding fragments thereof, bind to one or more of domains 1-3 of human sFlt-1.

It is observed that the ability of an antibody to deplete sFlt-1 from blood or a component thereof is not necessarily dependent on binding affinity, and may be influenced by the region of sFlt-1 to which the antibody binds. In certain embodiments of the invention, the anti-sFlt-1 antibodies or sFlt-1 binding fragments thereof compete for binding with an antibody which comprises one, two, or three heavy chain CDRs having SEQ ID NO:18, SEQ ID NO:20, and SEQ ID NO:22 and one, two, or three light chain CDRs having SEQ ID NO:24, SEQ ID NO:26, and SEQ ID NO:28. In certain embodiments, the anti-sFlt-1 antibodies compete for binding with an antibody which comprises one, two, or three heavy chain CDRs having substantially the same sequence as SEQ ID NO:18, SEQ ID NO:20, and SEQ ID NO:22 and one, two, or three light chain CDRs having substantially the same sequence as SEQ ID NO:24, SEQ ID NO:26, and SEQ ID NO:28. In some embodiments, the anti-sFlt-1 antibodies or binding fragments thereof compete for binding with an antibody which comprises at least one variable region with an amino acid sequence selected from SEQ ID NOS: 30 and 32, or a sequence at least 85% or at least 90% identical thereto.

In certain embodiments of the invention, the anti-sFlt-1 antibodies or sFlt-1 binding fragments thereof compete for binding with an antibody which comprises one, two, or three heavy chain CDRs having SEQ ID NO:2, SEQ ID NO:4, and SEQ ID NO:6 and one, two, or three light chain CDRs having SEQ ID NO:8, SEQ ID NO:10, and SEQ ID NO:12. In certain embodiments, the anti-sFlt-1 antibodies compete for binding with an antibody which comprises one, two, or three heavy chain CDRs having substantially the same sequence as SEQ ID NO:2, SEQ ID NO:4, and SEQ ID NO:6 and one, two, or three light chain CDRs having substantially the same sequence as SEQ ID NO:8, SEQ ID NO:10, and SEQ ID NO:12. In some embodiments, the anti-sFlt-1 antibodies or binding fragments thereof compete for binding with an antibody which comprises at least one variable region with an amino acid sequence selected from SEQ ID NOS: 14 and 16, or a sequence at least 85% or at least 90% identical thereto.

In certain embodiments, the pregnancy-related hypertensive disorder is eclampsia or pre-eclampsia. In certain embodiments, the pregnancy-related hypertensive disorder is pre-eclampsia. In certain embodiments, the sFlt-1 related disorder is kidney disease.

In certain embodiments, the blood or a component thereof is plasma and the method comprises removing a volume of the subject's blood and separating the blood into plasma and cellular components before contacting the plasma with anti-sFlt-1 antibodies, or sFlt-1 antigen binding fragments thereof, bound to a solid support.

In certain embodiments, the subject is a pregnant human, a post-partum human, or a non-human (e.g., a cow, a horse, a sheep, a pig, a goat, a dog, or a cat). In certain embodiments, the subject is a pregnant human or a post-partum human. In certain embodiments, the subject is a pregnant human.

The present invention provides a system comprising anti-sFlt-1 antibodies, or sFlt-1 antigen binding fragments thereof, or sFlt-1 ligands, bound to a solid support, first means for conveying blood from a subject to the anti-sFlt-1 antibodies, or sFlt-1 antigen binding fragments thereof, or sFlt-1 ligands, bound to the solid support so as to contact the blood with the anti-sFlt-1 antibodies, or sFlt-1 antigen binding fragments thereof, and thereby remove sFlt-1 from the blood, and second means for conveying the blood to the subject following contact of the blood with the anti-sFlt-1 antibodies, or sFlt-1 antigen binding fragments thereof.

In certain embodiments of the present invention, plasma, rather than blood, is contacted with anti-sFlt-1 antibodies, or sFlt-1 antigen binding fragments thereof, or sFlt-1 ligands, bound to a solid support, in order to treat or prevent a pregnancy-related hypertensive disorder. Accordingly, in certain embodiments, the first means includes a device for separating the subject's blood into plasma and cellular components.

In certain embodiments, the first means comprises an access device, such as a catheter, needle, cannula, or the like, inserted into a blood vessel of the subject, for accessing the subject's blood system, a conduit system, such as tubing, piping, hollow fibers, or the like, which fluidly connects the access device to the anti-sFlt-1 antibodies, or sFlt-1 antigen binding fragments thereof, bound to the solid support, thereby allowing the subject's blood to flow to and contact the anti-sFlt-1 antibodies, or sFlt-1 antigen binding fragments thereof, and, optionally, a pump (e.g., a peristaltic pump) or the like, for moving blood from the subject through the access device and conduit system to the anti-sFlt-1 antibodies, or sFlt-1 antigen binding fragments thereof.

In certain embodiments, the second means comprises a conduit system, such as tubing, piping, hollow fibers, or the like, and a return device, such as a catheter, needle, cannula, or the like, where the return device is inserted into a blood vessel (e.g., a vein) of the subject, where the conduit system fluidly connects the blood or plasma in contact with the anti-sFlt-1 antibodies, or sFlt-1 antigen binding fragments thereof, or sFlt-1 ligands, to the return device so as to allow for the return of the blood or plasma to the subject. Optionally, the second means also comprises a pump (e.g., a peristaltic pump) or the like, for moving the blood or plasma from the anti-sFlt-1 antibodies, or sFlt-1 antigen binding fragments thereof, or sFlt-1 ligands, through the conduit system to the return device. This pump or the like may be the same pump or the like that is part of the first means or, alternatively, the motive force for the second means for conveying the blood or plasma to the subject may be a separate pump or the like, specific to the second means.

In certain embodiments, the device for separating a subject's blood into plasma and cellular components is a centrifuge or an apheresis device, e.g., a plasmapheresis device.

In certain embodiments, the first and/or second means may also comprise one or more sensors for determining the pressure and/or the flow rate of the blood in the conduit system.

The present invention also provides a column containing anti-sFlt-1 antibodies, or sFlt-1 binding fragments thereof, or sFlt-1 ligands, bound to a solid support, where the column is suitable for use in treating or preventing a pregnancy-related hypertensive disorder such as eclampsia or pre-eclampsia.

DETAILED DESCRIPTION OF THE INVENTION

Figure 1:
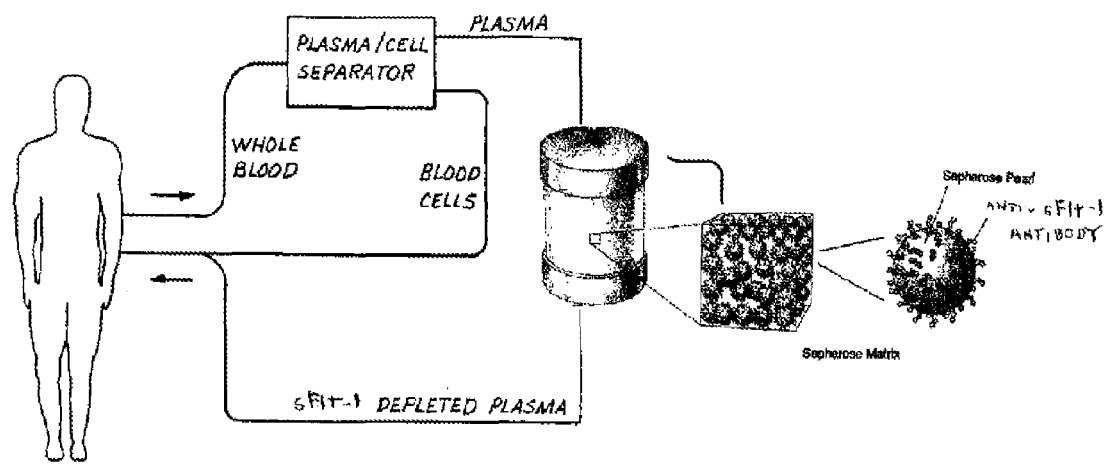
FIG. 1 shows a schematic depiction of one embodiment of the present invention where blood from a subject is separated into plasma and cellular components, the cellular components are returned to the subject, the plasma is conveyed to a column filled with SEPHAROSE® beads to which anti-sFlt-1antibodies have been attached such that contact with the anti-sFlt-1antibodies depletes the plasma of sFlt-1, and the sFlt-1-depleted plasma is returned to the subject.

The present invention provides a method of treating or preventing an sFlt-1-related disease or disorder comprising providing ex vivo to the subject anti-sFlt-1 binding substances, including but not limited to sFlt-1 ligands and binding proteins, anti-sFlt-1 antibodies, and sFlt-1 binding fragments thereof, in an amount sufficient and for a time sufficient to decrease the subject's blood levels of sFlt-1. In one embodiment, the invention provides a method of treating or preventing a pregnancy-related hypertensive disorder in a subject having or at risk of developing a pregnancy-related hypertensive disorder and thus in need of treatment or prevention for a pregnancy-related hypertensive disorder comprising providing ex vivo to the subject anti-sFlt-1 binding substances, including but not limited to sFlt-1 ligands and binding proteins, anti-sFlt-1 antibodies, and sFlt-1 binding fragments thereof, in an amount sufficient and for a time sufficient to decrease the subject's blood levels of sFlt-1, thereby treating or preventing the pregnancy-related hypertensive disorder in the subject. In another embodiment, the invention provides a method of treating pre-term labor. sFlt-1 levels are typically elevated during the last several weeks of a normal pregnancy, and may not be accompanied by a hypertensive disorder. Accordingly, the invention is used to treat non-hypertensive sFlt-1-related disorders of late stage pregnancy and labor or prophylactically to avoid such disorders. In another embodiment, the invention provides a method of treating or preventing chronic kidney disease.

"Soluble Flt-1 (sFlt-1)" (also known as sVEGF-R1) refers to a soluble form of the Flt-1 receptor that is identical or homologous to the protein defined by GenBank accession number AF063657, and has sFlt-1 biological activity. The biological activity of sFlt-1 may be assayed using any standard method, for example, by assaying sFlt-1 binding to VEGF. sFlt-1 lacks the transmembrane domain and the cytoplasmic tyrosine kinase domain of the Flt-1 receptor. sFlt-1 can bind to VEGF and PlGF with high affinity, but it cannot induce proliferation or angiogenesis and is therefore functionally different from the Flt-1 and KDR receptors. sFlt-1 was initially purified from human umbilical endothelial cells and later shown to be produced by trophoblast cells in vivo. As used herein, sFlt-1 includes any sFlt-1 family member or isoform. Non-limiting examples include sFlt-1 isoforms that are recognized to be splice variants. The splice variants have a common transcription start site, but do not contain all 30 spliced exons that encode Flt-1. One isoform is encoded by an mRNA having the first 13 exons followed by a portion of intron 13 and a poly(A) signal sequence and contains the first six Ig-like domains, but not the seventh Ig-like domain, transmembrane domain, or intracellular domain. (GenBank Accession No. AF063657; Kendall et al., Proc. Natl. Acad. Sci. USA 1993, 90:10705-9). Another isoform is encoded by an mRNA having the first 14 exons followed by a new alternatively spliced terminal exon 15 and a poly(A) signal sequence. The isoform is truncated in the seventh extracellular Ig-like domain (GenBank Accession No. AI188382; Thomas et al., 2007, FASEB J. 21:3885-3895). Several other alternatively spliced mRNAs and their translation products have also been reported or predicted. Each of these proteins contain unique C-terminal sequences that include amino acids encoded by the alternatively spliced 3' end of the mRNA up to the first translation termination codon. sFlt-1 can also mean degradation products or fragments that result from enzymatic cleavage of the Flt-1 receptor where such degradation products or fragments maintain sFlt-1 biological activity. In one example, specific metalloproteinases released from the placenta may cleave the extracellular domain of Flt-1 receptor to release the N-terminal portion of Flt-1 into circulation.

"Ex vivo" refers to practicing the methods of treatment or prevention disclosed herein outside the body of a subject, i.e., extracorporeally, whereby the subject's blood or blood component (e.g., plasma) is contacted with anti-sFlt-1 antibodies or sFlt-1 binding fragments thereof outside the body of the subject.

"Anti-sFlt-1 antibody" refers to an antibody that is capable of binding to sFlt-1. "sFlt-1 binding fragment" of an anti-sFlt-1 antibody refers to a portion of an anti-sFlt-1 antibody that retains the ability to bind sFlt-1.

"sFlt-1 ligand" refers to a growth factor or derivative thereof that binds to sFlt-1. Naturally occurring sFlt-1 ligands include, without limitation, vascular endothelial growth factor (VEGF), and placenta growth factor (PlGF). The VEGF is preferably VEGF-A or VEGF-B. VEGF includes its isoforms, including without limitation, $VEGF_{121}$, $VEGF_{165}$, and $VEGF_{189}$. PlGF includes it isoforms, including without limitation, PlGF-1, PlGF-2, PlGF-3, and PlGF-4. Derivatives include without limitation VEGF and PlGF fusion proteins and sequence variants of VEGF and PlGF that bind to sFlt-1.

"sFlt-1 binding substances" include antibodies, antibody fragments, ligands, and any other binding molecules (e.g., natural or synthetic proteins, polypeptides, and polymers) that selectively bind to sFlt-1.

The antibodies of the invention are effective to efficiently deplete sFlt-1 in blood or plasma from a subject. The sFlt-1 can be soluble, or in microparticles circulating in the bloodstream. According to the invention, heparin can be administered to the subject to release tissue-bound sFlt-1, enhancing ex vivo depletion of sFlt-1 and minimizing the pool of non-circulating sFlt-1 left in the subject.

Non-limiting examples of antibody sequences are provided. The invention provides an isolated sFlt-1 antibody (including sFlt-1 binding fragments thereof) which comprises one, two, or three heavy chain CDRs having SEQ ID NO:18, SEQ ID NO:20, and SEQ ID NO:22 and one, two, or three light chain CDRs having SEQ ID NO:24, SEQ ID NO:26, and SEQ ID NO:28. The invention also provides an sFlt-1 antibody comprising one, two, or three heavy chain CDRs that are substantially identical to SEQ ID NO:18, SEQ ID NO:20, and SEQ ID NO:22 and one, two, or three light chain CDRs that are substantially identical to SEQ ID NO:24, SEQ ID NO:26, and SEQ ID NO:28. In certain of the embodiments, the anti-sFlt-1 antibodies or binding fragments thereof comprise at least one variable region with an amino acid sequence selected from SEQ ID NOS:30 and 32, or a sequence at least 85% at least 90%, at least 95%, at least 97%, at least 98%, or at least 99%, identical thereto.

The invention further provides an isolated sFlt-1 antibody which comprises one, two, or three heavy chain CDRs having SEQ ID NO:2, SEQ ID NO:4, and SEQ ID NO:6 and one, two, or three light chain CDRs having SEQ ID NO:8, SEQ ID NO:10, and SEQ ID NO:12, as well as an sFlt-1 antibody comprising one, two, or three heavy chain CDRs that are substantially identical to SEQ ID NO:2, SEQ ID NO:4, and SEQ ID NO:6 and one, two, or three light chain CDRs that are substantially identical to SEQ ID NO:8, SEQ ID NO:10, and SEQ ID NO:12. In certain of the embodiments, the anti-sFlt-1 antibodies or binding fragments thereof comprise at least one variable region with an amino acid sequence selected from SEQ ID NOS: 14 and 16, or a sequence at least 85% at least 90%, at least 95%, at least 97%, at least 98%, or at least 99%, identical thereto.

"Identity" refers to the number or percentage of identical positions shared by two amino acid or nucleic acid sequences, taking into account the number of gaps, and the length of each gap, which need to be introduced for optimal alignment of the two sequences. "Substantially identical" means an amino acid sequence that which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein. Preferably, the amino acid sequence is at least 80%, more preferably at least about 85%, and most preferably at least about 90% similar to another amino acid sequence. Methods and computer programs for determining sequence similarity are publically available, including, but not limited to, the GCG program package (Devereux et al., Nucleic Acids Research 12: 387, 1984), BLASTP, BLASTN, FASTA (Altschul et al., J. Mol. Biol. 215:403 (1990), and the ALIGN program (version 2.0). The well-known Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0 at http://www.ncbi.nlm.nih.gov/blast/). In comparing sequences, these methods account for various substitutions, deletions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

It is observed herein that the ability of an antibody to deplete sFlt-1 from blood or a component thereof is not necessarily dependent on binding affinity, but also can depends on certain other characteristics, such as the domains or epitope of sFlt-1 to which the antibody binds. In certain embodiments of the invention, the anti-sFlt-1 antibodies or sFlt-1 binding fragments of the invention compete for binding with an antibody which comprises one, two, or three heavy chain CDRs having SEQ ID NO:18, SEQ ID NO:20, and SEQ ID NO:22 and one, two, or three light chain CDRs having SEQ ID NO:24, SEQ ID NO:26, and SEQ ID NO:28. In certain embodiments, the anti-sFlt-1 antibodies compete for binding with an antibody which comprises one, two, or three heavy chain CDRs having substantially the same sequence as SEQ ID NO:18, SEQ ID NO:20, and SEQ ID NO:22 and one, two, or three light chain CDRs having substantially the same sequence as SEQ ID NO:24, SEQ ID NO:26, and SEQ ID NO:28. In some such embodiments, the anti-sFlt-1 antibodies or binding fragments thereof compete for binding with an antibody which comprises at least one variable region with an amino acid sequence selected from SEQ ID NOS: 30 and 32, or a sequence at least 85% or at least 90% identical thereto.

In certain embodiments of the invention, the anti-sFlt-1 antibodies or sFlt-1 binding fragments thereof compete for binding with an antibody which comprises one, two, or three heavy chain CDRs having SEQ ID NO:2, SEQ ID NO:4, and SEQ ID NO:6 and one, two, or three light chain CDRs having SEQ ID NO:8, SEQ ID NO:10, and SEQ ID NO:12. In certain embodiments, the anti-sFlt-1 antibodies compete for binding with an antibody which comprises one, two, or three heavy chain CDRs having substantially the same sequence as SEQ ID NO:2, SEQ ID NO:4, and SEQ ID NO:6 and one, two, or three light chain CDRs having substantially the same sequence as SEQ ID NO:8, SEQ ID NO:10, and SEQ ID NO:12. In some such embodiments, the anti-sFlt-1 antibodies or binding fragments thereof compete for binding with an antibody which comprises at least one variable region with an amino acid sequence selected from SEQ ID NOS:14 and 16, or a sequence at least 85% or at least 90% identical thereto.

The following Table 1 lists the SEQ ID NOS: corresponding to nucleotide and amino acid sequences of the variable domains and CDRs of anti-sFlt-1 antibodies "101" and "102" disclosed herein.

TABLE 1

Antibody SEQ ID NOS

| | Antibody Designation | | | |
|---|---|---|---|---|
| | 101 | | 102 | |
| | nucleotide sequence | amino acid sequence | nucleotide sequence | amino acid sequence |
| CDR1H | 1 | 2 | 17 | 18 |
| CDR2H | 3 | 4 | 19 | 20 |
| CDR3H | 5 | 6 | 21 | 22 |
| CDR1L | 7 | 8 | 23 | 24 |
| CDR2L | 9 | 10 | 25 | 26 |
| CDR3L | 11 | 12 | 27 | 28 |
| VH | 13 | 14 | 29 | 30 |
| VL | 15 | 16 | 31 | 32 |

In certain embodiments, the anti-sFlt-1 antibodies, or sFlt-1 binding fragments thereof, bind to an epitope on human sFlt-1 that is bound by one or more of the antibodies referred to herein as 101, 102, or AG10A-D. Two antibodies compete (i.e., bind to the same or overlapping epitope) if each competitively inhibits (blocks) binding of the other to the antigen. That is, a 1×, 5×, 10×, 20×, or 100× excess of one antibody inhibits binding of the other by at least 50%, preferably 75%, 90%, or even 99% as measured in a competitive binding assay (see, e.g., Junghans et al., Cancer Res. 50:1495, 1990). Additional methods of determining whether one antibody binds to the same or overlapping epitope as another antibody are well known in the art.

In certain embodiments, an anti-sFlt-1 antibody, or sFlt-1 binding fragment thereof, binds human sFlt-1 but does not bind human Flt-1. In certain embodiments, an anti-sFlt-1 antibody, or sFlt-1 binding fragment thereof, that binds sFlt-1 recognizes the extracellular domain of Flt-1. In certain embodiments, an anti-sFlt-1 antibody, or sFlt-1 binding fragment thereof, recognizes an epitope in sFlt-1 that is not present in Flt-1. In certain embodiments, such an epitope not present in Flt-1 includes amino acids from the carboxy terminus of sFlt-1. In certain embodiments, such an epitope not present in Flt-1 is a discontinuous epitope or a conformational epitope of sFlt-1. In certain embodiments, the anti-sFlt-1 antibodies, or sFlt-1 binding fragments thereof, bind to the ligand binding site of Flt-1.

According to the invention, in certain embodiments, the anti-sFlt-1 antibodies, or sFlt-1-binding fragments thereof, are particularly suitable for administration to a subject. For example, the antibodies can be modified to minimize immunogenicity and/or hypersensitivity in a subject. Such modifications can provide an additional safety factor in the event that antibodies are leached from a column or other solid support used for ex vivo the treatment of a subject. Further, in certain embodiments, the sFlt-1 antibodies, or sFlt-1-binding fragments thereof, can be administered in vivo to treat eclampsia or pre-eclampsia. Thus, for both ex vivo and in vivo treatment, antibodies used according to the invention include chimeric or humanized antibodies, as well as antigen binding fragments of the anti-sFlt-1 antibodies. Chimeric antibody 10A ($V_H$: SEQ ID NO:35; $V_L$: SEQ ID NO:36) comprises the variable region of antibody 102 and a human IgG1 constant region. The antibodies may also be modified to minimize or eliminate other effects. For example the constant region of chimeric antibody 10B ($V_H$: SEQ ID NO:37; $V_L$: SEQ ID NO:36), provided herein, includes the mutation N298Q, which prevents glycosylation. Antibodies containing this mutation are deficient in effector functions, such as complement activation and binding to Fc. Chimeric antibody AG10C ($V_H$: SEQ ID NO:38; $V_L$: SEQ ID NO:36) includes the mutation I254A, which disrupts binding of the antibody to neonatal Fc receptor (FcRn). The FcRn receptor facilitates transport of maternal IgG across the placenta to the fetus. Accordingly, AG10C would bind sFlt-1 in the treatment subject, but not be transported to the growing fetus. In an embodiment of the invention, antibodies for ex vivo or in vivo administration include both mutations (e.g., chimeric antibody AG10D; $V_H$: SEQ ID NO:39; $V_L$: SEQ ID NO:36).

The anti-sFlt-1 antibodies, or sFlt-1 binding fragments thereof, or sFlt-1 ligands, are used to neutralize the activity of sFlt-1 and one possible mechanism is through direct blocking of the binding sites on sFlt-1 for growth factors such as VEGF or PlGF. However, other mechanisms are also possible. For example, the anti-sFlt-1 antibodies, or sFlt-1 binding fragments thereof, may bind to a site on sFlt-1 such that binding of VEGF or PlGF to sFlt-1 is not blocked. In either case, the sFlt-1 is removed from the blood or plasma by virtue of being captured by the solid-support bound anti-sFlt-1 antibodies, or sFlt-1 binding fragments thereof, and is no longer available to bind to, and thus reduce the concentration of, free growth factors such as VEGF or PlGF in the blood or plasma. Further, when captured by solid support-bound antibodies or binding fragments thereof, sFlt-1 is no longer available to form heterodimers with membrane-bound Flt-1 or KDR.

The anti-sFlt-1 antibodies of the invention bind to one or more extracellular Ig-like domains of Flt-1. In certain embodiments an anti-sFlt-1 antibody, or sFlt-1 binding fragment thereof, binds to one or more of domains 1-3 of sFlt-1 and blocks ligand binding. The domain structure of Flt-1 has been described. (See, e.g., Davis-Smyth et al., 1996, EMBO Journal, 15(18):4919-27). For example, the first Ig-like domain extends from about Pro32 to about Ile128. The second Ig-like domain extends from about Pro134 to about Thr226. The third Ig-like domain extends from about Val232 to about Lys331. The fourth Ig-like domain, which is thought to be critical for receptor dimer formation, extends from about Phe333 to about Pro428. The fifth Ig-like domain extends from about Tyr431 to about Thr553. The sixth Ig-like domain extends from about Gly558 to about Arg656. The seventh Ig-like domain extends from about Tyr662 to about Thr751.

When such an anti-sFlt-1 antibody, or sFlt-1 binding fragment thereof, or sFlt-1 ligand, is employed in the ex vivo methods disclosed herein, it binds to sFlt-1 molecules that are not bound by sFlt-1 ligand and removes those sFlt-1 molecules from blood or plasma. In other embodiments, the anti-sFlt-1 antibody, or sFlt-1 binding fragment thereof, binds to one or more of domains 1-3 of sFlt-1 and does not block ligand binding. In certain other embodiments, the anti-sFlt-1 antibody, or sFlt-1 binding fragment thereof, binds to sFlt-1 and bound ligand is displaced. Thus, in certain embodiments, the amount of sFlt-1 in a subject is reduced without a substantial reduction of sFlt-1 ligand.

In certain embodiments, the anti-sFlt-1 antibodies, or sFlt-1 binding fragments thereof, or sFlt-1 ligands, bind to sFlt-1 so as to prevent dimerization. Binding of Flt-1 ligand to Flt-1 is understood to be cooperative, such that a stable receptor-ligand complex includes a ligand dimer bound to a receptor dimer. Accordingly, blocking receptor dimerization destabilizes receptor-ligand interactions. When anti-sFlt-1 antibodies, or sFlt-1 binding fragments thereof, or sFlt-1 ligands, that block dimerization are employed in the ex vivo methods disclosed herein, such antibodies or binding fragments bind to sFlt-1 and reduce the amount of circulating sFlt-1. Thus, the amount of sFlt-1 in a subject is reduced without a substantial reduction of sFlt-1 ligand. Since dimerization of bound sFlt-1 is blocked, the stability of any sFlt-1 monomer with ligand is reduced. Thus, any reduction of sFlt-1 ligand in the subject may be insubstantial.

In certain embodiments, the anti-sFlt-1 antibodies, or sFlt-1 binding fragments thereof, bind to sFlt-1 but do not substantially block or inhibit ligand binding or sFlt-1 dimerization. In certain embodiments, the anti-sFlt-1 antibodies, or sFlt-1 binding fragments thereof, bind to an epitope that is present in all isoforms of sFlt-1.

In one embodiment, the anti-sFlt-1 antibodies, or sFlt-1 binding fragments thereof, or sFlt-1 ligands, bind to Ig-like domain 1 of sFlt-1. In another embodiment, the anti-sFlt-1 antibodies, or sFlt-1 binding fragments thereof, or sFlt-1 ligands, bind to Ig-like domain 2 of sFlt-1. In another embodiment, the anti-sFlt-1 antibodies, or sFlt-1 binding fragments thereof, or sFlt-1 ligands, bind to Ig-like domain 3 of sFlt-1. In yet another embodiment, the anti-sFlt-1 antibodies, or sFlt-1 binding fragments thereof, or sFlt-1 ligands, bind to Ig-like domains 1-2 of sFlt-1. In another embodiment, the anti-sFlt-1 antibodies, or sFlt-1 binding fragments thereof, or sFlt-1 ligands, bind to Ig-like domains 2-3 of sFlt-1. In still another embodiment, the anti-sFlt-1 antibodies, or sFlt-1 binding fragments thereof, or sFlt-1 ligands, bind to Ig-like domains 1 and 3 of sFlt-1.

Disclosed herein are anti-sFlt-1 antibodies suitable for use in the present methods and systems (e.g., 101, 102, AG10A-D). Based on these anti-sFlt-1 antibodies, it would be a routine matter for those skilled in the art to design and produce additional anti-sFlt-1 antibodies for use in the present methods and systems by, e.g., designing and producing additional anti-sFlt-1 antibodies that comprise the variable region sequences and/or CDRs of the anti-sFlt-1 antibodies disclosed herein. Moreover, it would be a routine matter to design additional anti-sFlt-1 antibodies that comprise variable region sequences or CDRs that have certain specified levels of identity in amino acid sequence to the variable region sequences or CDRs of the anti-sFlt-1 antibodies disclosed herein.

In designing and producing additional anti-sFlt-1 antibodies, those skilled in the art may be guided by certain well known features of antibodies. The structure of typical naturally occurring antibodies is well known and includes two identical heavy chains and two identical light chains, with each light chain covalently linked to a heavy chain by an interchain disulfide bond. The two heavy chains are linked to one another by additional disulfide bonds. Individual heavy and light chains can fold into domains having similar sizes (110-125 amino acids) and structures, but different functions. Light chains can comprise one variable domain ($V_L$) and/or one constant domain ($C_L$). Heavy chains can also comprise one variable domain ($V_H$) and/or three or four constant domains ($C_H1$, $C_H2$, $C_H3$ and $C_H4$), depending on the class or isotype of antibody. In humans, the isotypes are IgA, IgD, IgE, IgG, and IgM, with IgA and IgG further subdivided into subclasses or subtypes ($IgA_{1-2}$ and $IgG_{1-4}$).

As one might expect from their name, variable domains show considerable amino acid sequence variability from one antibody to the next. This variability is generally greatest at the location of the antigen-binding sites. Three regions, called hypervariable or complementarity-determining regions (CDRs), are found in each of $V_L$ and $V_H$, which are supported by less variable regions called framework variable regions.

It has been found to be convenient to consider certain portions of antibody molecules individually. The portion of an antibody consisting of $V_L$ and $V_H$ domains is designated Fv (fragment variable) and constitutes the antigen-binding site. An antibody fragment containing a $V_L$ domain and a $V_H$ domain on one polypeptide chain is referred to as a single chain Fv (scFv) and generally contains the N terminus of one domain and the C terminus of the other domain joined by a flexible linker (see, e.g., U.S. Pat. No. 4,946,778 and International Patent Publication WO 88/09344.

For certain embodiments disclosed herein, it may be advantageous to employ scFv fragments because scFv fragments lack some or all of the constant domains of whole antibodies. Therefore, they can overcome some of the side-effects associated with the use of whole antibodies. For example, scFv fragments tend to be free of certain undesired interactions between heavy-chain constant regions and other biological molecules.

In certain embodiments, the solid support may have attached multivalent single chain antibodies, where multiple single chain antibodies, each single chain having one $V_H$ and one $V_L$ domain covalently linked by a first peptide linker, are covalently linked by at least one or more second peptide linkers to form a multivalent single chain antibody. Each chain of a multivalent single chain antibody includes a variable light chain fragment and a variable heavy chain fragment, and is linked by the second peptide linker to at least one other chain. The second peptide linker is preferably composed of at least fifteen and fewer than one hundred amino acid residues.

In certain embodiments, the solid support may have attached diabodies, where two single chain antibodies are combined to form a diabody. Diabodies have two chains and two binding sites, each specific for sFlt-1. Each chain of the diabody includes a $V_H$ domain connected to a $V_L$ domain.

The domains are connected with linkers that are short enough to prevent pairing between domains on the same chain, thus driving the pairing between complementary domains on different chains to recreate the two antigen-binding sites.

In certain embodiments, the solid support may have attached triabodies, where three single chain antibodies are combined to form a triabody. In triabodies, the amino acid terminus of a $V_L$ or $V_H$ domain is directly fused to the carboxyl terminus of a $V_L$ or $V_H$ domain, i.e., without any linker sequence. The triabody has three Fv heads with the polypeptides arranged in a cyclic, head-to-tail fashion.

In certain embodiments, the solid support may have attached Fab fragments. Fab fragments are fragments of an antibody consisting of $V_L$ $C_L$ $V_H$ and $C_H1$ domains. Those generated following papain digestion simply are referred to as Fab and lack the heavy chain hinge region. Following pepsin digestion, various Fabs retaining the heavy chain hinge are generated. Those divalent fragments with the interchain disulfide bonds intact are referred to as $F(ab')_2$, while a monovalent Fab' results when the disulfide bonds are not retained.

Thus, anti-sFlt-1 antibodies, and sFlt-1 binding fragments thereof, for use in the methods and systems disclosed herein include, but are not limited to, naturally occurring antibodies, bivalent fragments such as $(Fab')_2$, monovalent fragments such as Fab, single chain antibodies, single chain Fv (scFv), single domain antibodies, multivalent single chain antibodies, diabodies, triabodies, and the like that bind sFlt-1.

In certain embodiments, specificity of antibodies, or fragments thereof, can be determined based on affinity and/or avidity. Affinity, represented by the equilibrium constant for the dissociation of an antigen with an antibody ($K_d$), measures the binding strength between an antigenic determinant and an antibody-binding site. Avidity is the measure of the strength of binding between an antibody with its antigen. Avidity is related to both the affinity between an epitope with its antigen binding site on the antibody, and the valence of the antibody, which refers to the number of antigen binding sites of a particular epitope. Antibodies typically bind with a dissociation constant ($K_d$) of $10^{-5}$ to $10^{-11}$ liters/mol. Any $K_d$ greater than $10^{-4}$ liters/mol is generally considered to indicate nonspecific binding. The lesser the value of the $K_d$, the stronger the binding strength between an antigenic determinant and the antibody binding site.

In certain embodiments, the anti-sFlt-1 antibodies, or sFlt-1 binding fragments, bind sFlt-1 with a dissociation constant ($K_d$) of about $10^{-5}$ to $10^{-11}$ liters/mol, about $10^{-6}$ to $10^{-10}$ liters/mol, or about $10^{-7}$ to $10^{-9}$ liters/mol. In certain embodiments, anti-sFlt-1 antibodies, or sFlt-1 binding fragments, bind to sFlt-1 with a dissociation constant ($K_d$) of at least about $10^{-5}$ liters/mol, at least $10^{-6}$ liters/mol, at least $10^{-7}$ liters/mol, at least $10^{-8}$ liters/mol, at least $10^{-9}$ liters/mol, at least $10^{-10}$ liters/mol, or at least $10^{-11}$ liters/mol. In certain embodiments, the $K_d$ is from $10^{-9}$ liters/mol to $10^{-10}$ liters/mol. In certain embodiments, embodiments, the $K_d$ is from $10^{-10}$ liters/mol to $10^{-11}$ liters/mol.

Anti-sFlt-1 antibodies suitable for use in the methods and systems disclosed herein further include those for which binding characteristics have been improved by direct mutation, methods of affinity maturation, phage display, or chain shuffling. Affinity and specificity can be modified or improved by mutating CDRs and screening for antigen binding sites having the desired characteristics (see, e.g., Yang et al., J. Mol. Biol., 254: 392-403 (1995)). CDRs can be mutated in a variety of ways. One way is to randomize individual residues or combinations of residues so that in a population of otherwise identical antigen binding sites, all twenty amino acids are found at particular positions. Alternatively, mutations may be induced over a range of CDR residues by error prone PCR methods (see, e.g., Hawkins et al., J. Mol. Biol., 226: 889-896 (1992)). For example, phage display vectors containing heavy and light chain variable region genes can be propagated in mutator strains of *E. coli* (see, e.g., Low et al., J. Mol. Biol., 250: 359-368 (1996)). These methods of mutagenesis are illustrative of the many methods known to one of skill in the art.

Anti-sFlt-1 antibodies can be obtained by standard hybridoma technology (e.g., Harlow & Lane, ed., Antibodies: A Laboratory Manual, Cold Spring Harbor, 211-213 (1998), which is incorporated by reference herein) or by using transgenic mice (e.g., KM mice, originally from Medarex, San Jose, Calif.) that produce human immunoglobulin gamma heavy and kappa light chains. In certain mice known in the art, a substantial portion of the human antibody producing genome is inserted into the genome of the mice, and the mice are rendered deficient in the production of endogenous murine antibodies. Such mice may be immunized with part or all of sFlt-1 (e.g., human sFlt-1), optionally in a suitable adjuvant, e.g., complete or incomplete Freund's adjuvant.

Methods for the preparation of antibodies suitable for use in the methods and systems disclosed herein are well known in the art and are described, e.g., in U.S. Pat. No. 6,054,297; U.S. Pat. No. 5,821,337; U.S. Pat. No. 6,365,157; and U.S. Pat. No. 6,165,464; U.S. Patent Application Publication No. 2006/0067937; International Patent Publication WO 06/034507; which are incorporated herein by reference.

The anti-sFlt-1 antibodies suitable for use in the methods and systems disclosed herein may include polyclonal antibodies, monoclonal antibodies, humanized or chimeric antibodies, Fv fragments, single chain Fv fragments, Fab fragments, or $F(ab')_2$ fragments. In certain embodiments, the antibodies are mouse monoclonal antibodies. The anti-sFlt-1 antibodies may include a variety of antibody isotypes, such as IgG1, IgG2, IgG3, IgG4, IgM, IgA1, IgA2, secretory IgA, IgD, and IgE.

"Chimeric antibody" refers to a polypeptide comprising at least the antigen-binding portion of an antibody molecule linked to at least part of another protein (typically an immunoglobulin constant domain).

"Humanized antibody" refers to an antibody with a framework region (FR) having substantially the amino acid sequence of a human immunoglobulin and a complementarity determining region (CDR) having substantially the amino acid sequence of a non-human immunoglobulin (the "import" sequences). Generally, a humanized antibody has one or more amino acid residues introduced into it from a source that is non-human. The humanized antibody will usually comprise substantially all of at least one, and typically two, variable domains (Fab, Fab', $F(ab')_2$, Fabc, Fv) in which all or substantially all of the CDR regions correspond to those of a non-human immunoglobulin and all or substantially all of the FR regions are those of a human immunoglobulin or a human immunoglobulin consensus sequence. The humanized antibody optimally will comprise at least a portion of an immunoglobulin constant region (Fc), typically that of a human immunoglobulin. By "complementarity determining region (CDR)" is meant the three hypervariable sequences in the variable regions within each of the immunoglobulin light and heavy chains. By "framework region (FR)" is meant the sequences of amino acids located on either side of the three hypervariable sequences (CDR) of the immunoglobulin light and heavy chains. The FR and CDR regions of the humanized antibody need not correspond precisely to the parental sequences, e.g., the import CDR or the human or consensus human FR may be mutagenized by substitution, insertion, or deletion of at least one residue so that the CDR or FR residue at that site does not correspond to either the consensus or the import sequence. Such mutations, however, will not be extensive. Usually, at least 75%, preferably 90%, and most preferably at least 95% of the humanized antibody residues will correspond to those of the parental FR and CDR sequences.

The anti-sFlt-1 antibodies may be obtained directly from hybridomas which express the anti-sFlt-1 antibodies or may be cloned and recombinantly expressed in suitable host cells (e.g., CHO cells, NS/0 cells, HEK293 cells). Suitable host cells include plant cells, mammalian cells, and microorganisms such as E. coli and yeast. Alternatively, anti-sFlt-1 antibodies may be produced recombinantly in a transgenic non-human animal or plant, e.g., a transgenic mouse.

In certain embodiments, the anti-sFlt-1 antibodies may be modified prior to, or after, attachment to a solid support. Possible modifications include glycosylation, acetylation, pegylation, phosphorylation, amidation, derivatization with protecting or blocking groups, proteolytic cleavage, or linkage to a cellular ligand or other protein. In certain embodiments, the anti-sFlt-1 antibodies may contain one or more non-classical amino acids.

The anti-sFlt-1 antibodies, or antigen binding fragments thereof are suitable for ex vivo treatment of an sFlt-1-related disorder. Suitable means that the antibodies effectively reduce the concentration of sFlt-1 in a subject's blood or plasma when used in a effective amount for an effective time. For example, using a 50 ml/minute flow rate, 5 liters of plasma (approximately 2.5 human blood volumes) would be processed in 100 minutes. As exemplified herein, in one assay, antibody AG10B depleted 94% of sFlt-1 from a test solution using a flow rate of 1 ml/min applied to a 1 ml column. This is comparable to a 50 ml/min flow rate using a 50 ml column (and comparable to a residence time of 1 min). Another assay shows that sFlt-1 depletion in a test sample was only slightly reduced when the concentration of AG10B on the solid support was reduced from 0.8 mg/ml of beads to 0.4 mg/ml of beads.

For research purposes, columns of various dimensions containing 0.1-50 mL of Sepharose beads coupled with anti-sFlt-1 antibodies are tested for their ability to deplete recombinant sFlt-1 spiked into buffered solutions or animal serum or human plasma, or native sFlt-1 in amniotic fluid or blood plasma of preeclampsia patients. The sFlt-1 depletion experiments are conducted with columns containing anti-sFlt-1 antibody-coupled Sepharose beads at 0.025-20 mg of antibodies per 1 mL of beads (0.065-52 billion antibody molecules per single bead), at flow rates of 0.05-50 mL/min, at linear flow rates of 10-300 cm/hr, and residence times of 0.25-5 minutes. For these sFlt-1 depletion experiments, 1 to 400 times the column bed volumes of buffered solutions, serum or plasma containing sFlt-1 are applied to the columns at anti-sFlt-1 antibody:sFlt-1 ratios of 5:1 to 5,000:1 (w/w), or molar ratios of 1.25:1 to 1,250:1. Under these ranges of conditions, columns containing Sepharose beads coupled with anti-sFlt-1 antibodies deplete 50 to 100% of sFlt-1 in buffered solutions, serum or plasma.

For clinical treatments, columns of various dimensions containing 25 to 750 mL of Sepharose beads coupled with anti-sFlt-1 antibodies are used to deplete native sFlt-1 of various isoforms, alone or in complex with ligands such as VEGF or PlGF isoforms from blood plasma of patients suffering from diseases associated with high levels of sFlt-1 in blood, including preeclampsia. The columns used in clinical treatments contain anti-sFlt-1 antibody-coupled Sepharose beads at 0.1-5 mg of antibodies per 1 mL of beads (5-100 mg per 50 mL beads; 0.26-5.2 billion antibody molecules per single bead), at flow rates of 10-100 mL/min, at linear flow rates of 30-180 cm/hr, and residence times of 0.5-3 minutes. Patients with average weight will have about 8 Liters of blood circulating in their body (about 4 Liters of plasma). About 0.5-3 times the total body plasma volume (2-12 Liters of plasma), which corresponds to 40 to 240 times the column bed volumes of blood plasma (for a 50 mL column), containing 0.08-0.48 mg of native sFlt-1 (for a patient with 40 ng/mL sFlt-1 level in plasma) of various forms, are to be applied to the columns containing anti-sFlt-1 antibody-coupled beads at anti-sFlt-1 antibody:sFlt-1 ratios of 50:1 to 2,000:1 (w/w), or molar ratios of 12.5:1 to 500:1. Under these ranges of conditions, columns containing Sepharose beads coupled with anti-sFlt-1 antibodies are able to deplete 50 to 100% of sFlt-1 from plasma of patients with high sFlt-1 levels in their blood.

Thus, the invention provides a method treating or preventing a pregnancy-related hypertensive disorder in a subject comprising providing ex vivo to the subject an anti-sFlt-1 antibody, or sFlt-1 binding fragment thereof, wherein the anti-sFlt-1 antibody, or sFlt-1 binding fragment thereof, depletes at least 70%, or at least 80%, or at least 90%, or at least 95%, or at least 99%, or from 70% to 80%, or from 80% to 90%, or from 90% to 95%, or from 95% to 99% of sFlt-1 from human plasma in an in vitro analysis, when the anti-sFlt-1 antibody, or sFlt-1 binding fragment thereof, is attached to a solid support, and the molar antibody:sFlt-1 ratio is 500. In another embodiment, the invention provides a method treating or preventing a pregnancy-related hypertensive disorder in a subject comprising providing ex vivo to the subject an anti-sFlt-1 antibody, or sFlt-1 binding fragment thereof, wherein the anti-sFlt-1 antibody, or sFlt-1 binding fragment thereof, depletes at least 70%, or at least 80%, or at least 90%, or at least 95%, or at least 99%, or from 70% to 80%, or from 80% to 90%, or from 90% to 95%, or from 95% to 99% of sFlt-1 from human plasma in an in vitro analysis, when the anti-sFlt-1 antibody, or sFlt-1 binding fragment thereof, is attached to a solid support, and the antibody:sFlt-1 ratio is 250. In another embodiment, the invention provides a method treating or preventing a pregnancy-related hypertensive disorder in a subject comprising providing ex vivo to the subject an anti-sFlt-1 antibody, or sFlt-1 binding fragment thereof, wherein the anti-sFlt-1 antibody, or sFlt-1 binding fragment thereof, depletes at least 70%, or at least 80%, or at least 90%, or at least 95%, or at least 99%, or from 70% to 80%, or from 80% to 90%, or from 90% to 95%, or from 95% to 99% of sFlt-1 from human plasma in an in vitro analysis, when the anti-sFlt-1 antibody, or sFlt-1 binding fragment thereof, is attached to a solid support, and the molar antibody:sFlt-1 ratio is 100. In still other embodiments, at least 70%, or at least 80%, or at least 90%, or at least 95%, or at least 99%, or from 70% to 80%, or from 80% to 90%, or from 90% to 95%, or from 95% to 99% of sFlt-1 is depleted from human plasma in the in vitro analysis when the anti-sFlt-1 antibody, or sFlt-1 binding fragment thereof, is attached to a solid support, and the molar antibody:sFlt-1 ratio is 50, 25, or 12.5. The anti-sFlt-1 antibodies and sFlt-1 binding fragments thereof include those that bind to Flt-1 Ig-like domains 1-3 in various combinations, as well as antibodies that bind to Ig-like domains 4, 5, 6, or 7, either alone, or in combination, or in combination with Ig-like domains 2 and/or 3.

According to the analysis method, human serum is spiked with sFlt-1. As exemplified herein, an sFlt-1 protein consisting of domains 1-3 was used. When sFlt-1 antibodies against other domains or combinations of domains are tested, an sFlt-1 molecule containing the pertinent domains is used. Non-limiting examples of sFlt-1 molecules contain domains 1-3, domains 1-4, domains 1-5, domains 1-6, domains 1-7, domains 2-3, domains 2-4, domains 2-5, domains 2-6, or domains 2-7 of sFlt-1. (See, e.g., Barleon et al., 1997, J. Biol. Chem. 272:10382-88 for showing expression of various domains of sFlt-1). In certain embodiments the analysis is performed using Sepharose bead-bound anti-sFlt-1 antibodies or sFlt-1 binding fragments thereof mixed in sFlt-1-spiked plasma. In certain embodiments, the analysis is performed over a time period that replicates a residence time on a clinical column of 0.25, 0.5, 1, 1.5, 2, 2.5, 3, 4, or 5 minutes. Such an analysis can be performed using a solution of bead-bound anti-sFlt-1 antibodies or sFlt-1 binding fragments in a column and sFlt-1-spiked plasma applied at a flow rate to obtain a desired residence time. Alternatively, the analysis could be performed using sFlt-1 spiked in amniotic fluid, serum (e.g, horse serum), or a buffer solution (e.g., PBS), but plasma, particularly human plasma, is preferred. The analysis can be performed using anti-sFlt-1 antibodies or sFlt-1 binding fragments thereof bound to a column support (e.g., Sepharose beads) at various densities and sFlt-1 spiked in plasma at various concentrations. The anti-sFlt-1 antibodies or sFlt-1 binding fragments thereof can be linked to Sepharose beads in amounts of 0.025, 0.050, 0.1, 0.25, 0.5, 1, or 2 mg/bead. The flow rate can be 0.05, 0.1, 0.25, 0.5, 1, 2.5, 5, 10, 25, 50, or 100 ml/min, and linear flow rates can be 10, 20, 30, 50, 100, 150, 180, 240, or 300 cm/hr.

Antibodies of the invention are effective to efficiently deplete sFlt-1 in blood or plasma from a subject. The sFlt-1 can be soluble and/or in microparticles circulating in the bloodstream. In certain embodiments, when an antibody of the invention is attached to a solid support (e.g., Sepharose beads), and contacted with a solution containing sFlt-1 such that the antibody:sFlt-1 ratio is 50, the sFlt-1 antibody depletes (binds to) at least 70%, or at least 80%, or at least 90%, or at least 95% of sFlt-1. In certain embodiments, the sFlt-1 antibody depletes from 70% to 80%, of from 80% to 90%, or from 90% to 95%, of from 95 to 99% of sFlt-1. The solution can be blood, plasma, serum, or a buffer solution. In certain embodiments, when an antibody of the invention is attached to a solid support (e.g., Sepharose beads), and contacted with a solution containing sFlt-1 such that the antibody:sFlt-1 ratio is 100, the sFlt-1 antibody depletes at least 70%, or at least 80%, or at least 90%, or at least 95% of sFlt-1. In certain embodiments, the sFlt-1 antibody depletes from 70% to 80%, of from 80% to 90%, or from 90% to 95%, of from 95 to 99% of sFlt-1. In certain embodiments, when an antibody of the invention is attached to a solid support (e.g., Sepharose beads), and contacted with a solution containing sFlt-1 such that the antibody: sFlt-1 ratio is 250, the sFlt-1 antibody depletes at least 70%, or at least 80%, or at least 90%, or at least 95% of sFlt-1. In certain embodiments, the sFlt-1 antibody depletes from 70% to 80%, of from 80% to 90%, or from 90% to 95%, of from 95 to 99% of sFlt-1.

In certain embodiments, the anti-sFlt-1 antibody or sFlt-1 binding fragment is capable, under suitable conditions, of reducing the concentration of sFlt-1 in the subject's blood or plasma containing sFlt-1 to less than about 50 ng/ml, less than about 40 ng/ml, less than about 25 ng/ml, less than about 10 ng/ml, less than about 5 ng/ml, less than about 4 ng/ml, less than about 3 ng/ml, less than about 2 ng/ml, less than about 1 ng/ml, less than about 0.75 ng/ml, or less than about 0.5 ng/ml.

In certain embodiments, an sFlt-1 molecule is removed from blood plasma by immobilization to a solid support, for example, using an anti-sFlt-1 antibody, or sFlt-1 binding fragment thereof. When sFlt-1 is immobilized to a solid support, ligand binding is less favored compared to the case where sFlt-1 is free in solution. Accordingly, sFlt-1 levels are reduced in the subject, and any reduction of circulating sFlt-1 ligand may be insubstantial.

In certain embodiments, the anti-sFlt-1 antibodies are bound to a solid support where the solid support does not have anti-endoglin antibodies, or endoglin binding fragments thereof, bound to it. In certain embodiments of the methods disclosed herein, the methods do not substantially decrease the amount of endoglin in the subject's blood. In certain embodiments of the systems disclosed herein, the systems are not capable of significantly removing endoglin from the subject's blood.

In certain embodiments, the methods of the present invention comprise:
 (a) removing blood from the subject,
 (b) passing the blood or a component thereof over a solid support to which are attached anti-sFlt-1 antibodies, or sFlt-1 binding fragments thereof, or sFlt-1 ligands, to decrease the level of sFlt-1 in the blood or component thereof, and
 (c) returning the blood or component thereof to the subject's body.

In certain embodiments, the blood is separated into plasma and cellular components and only the plasma is contacted with the anti-sFlt-1 antibodies, or sFlt-1 binding fragments thereof, while the cellular components are returned to the subject without such contact or, in certain embodiments, disposed of rather than returned to the subject.

Accordingly, in certain embodiments, the method comprises removing a volume of the subject's blood, separating the blood into plasma and cellular components, bringing the plasma into contact with the anti-sFlt-1 antibodies, or sFlt-1 binding fragments thereof, to bind sFlt-1 in the plasma to the anti-sFlt-1 antibodies, or sFlt-1 binding fragments thereof, thereby decreasing the amount of sFlt-1 in the subject's plasma, returning the plasma to the subject, and, optionally, returning the cellular components to the subject.

When practicing the above embodiment, the cellular components may be returned to the subject at any time. That is, the cellular components may be returned to the subject before the plasma is contacted with the anti-sFlt-1 antibodies, or sFlt-1 binding fragments thereof, or the cellular components may be returned to the subject after the plasma is contacted with the anti-sFlt-1 antibodies, or sFlt-1 binding fragments thereof. In certain embodiments, the cellular components may be combined with the plasma after the plasma has been contacted with the anti-sFlt-1 antibodies, or sFlt-1 binding fragments thereof, and the combined cellular components and plasma are returned to the subject at the same time, through the same conduit system and/or the same return device.

In certain embodiments, the pregnancy-related hypertensive disorder is eclampsia or pre-eclampsia. In certain embodiments, the pregnancy-related hypertensive disorder is eclampsia. In certain embodiments, the disorder is chronic kidney disease.

In certain embodiments, the subject is a pregnant human, a post-partum human, or a pregnant or post-partum non-human (e.g., a cow, a horse, a sheep, a pig, a goat, a dog, or a cat). In certain embodiments, the subject is a pregnant human or a post-partum human. In certain embodiments, the subject is a pregnant human.

Optionally, the methods disclosed herein may be practiced on a subject who is being treated with standard pre-eclampsia or eclampsia therapies. Such standard therapies are known to the skilled artisan and include the methods described in U.S. Patent Application Publication No. US 2004/0126828; U.S. Patent Application Publication No. US 2005/0025762; U.S. Patent Application Publication No. US 2005/0170444; and U.S. Patent Application Publication No. US 2006/0067937 as well as in International Patent Publication WO 2004/008946; International Patent Publication WO 2005/077007; and International Patent Publication WO 06/034507.

The methods disclosed herein may be practiced using a combination of sFlt-1 binding substances. For example, two or more of anti-sFlt-1 antibodies, sFlt-1 binding fragments thereof, and sFlt-1 ligands may be used.

The methods disclosed herein may be practiced on a subject who is being treated with chronic hypertension medications. Medications used for the treatment of hypertension during pregnancy include methyldopa, hydralazine hydrochloride, or labetalol.

In certain embodiments, the methods of the present invention can further include the step of administering an anti-hypertensive compound to the subject. Such administration may be by conventional means, e.g., administering an oral dosage form comprising an anti-hypertensive compound.

In certain embodiments, the method of the present invention can further include administering a growth factor or cytokine, such as, without limitation, a VEGFR ligand, to the subject. In one embodiment, the growth factor is VEGF. In another embodiment, the growth factor is PlGF.

The methods disclosed herein may be practiced during pregnancy for the treatment or prevention of pre-eclampsia or eclampsia or after pregnancy to treat post-partum pre-eclampsia or eclampsia.

"Treating" refers to practicing the ex vivo methods disclosed herein for therapeutic purposes. To "treat" or to use for "therapy" refers to administering treatment to a subject already diagnosed as having or suffering from a pregnancy-related hypertensive disorder to improve the subject's condition. For example, the subject may be diagnosed as having or suffering from pre-eclampsia or eclampsia, based on identification of any of the characteristic symptoms described herein or based on measurement of the concentration of sFlt-1 in the subject's blood, as described herein.

"Prevent" refers to prophylactic treatment of a subject who is not yet ill, but who is susceptible to, or otherwise at risk for, developing a pregnancy-related hypertensive disorder, e.g., a subject who is determined to be at risk for developing pre-eclampsia or eclampsia.

"Pregnancy-related hypertensive disorder" refers to any condition or disease during pregnancy that is associated with or characterized by an increase in blood pressure. Included among these conditions and diseases are pre-eclampsia (including premature pre-eclampsia, severe pre-eclampsia), eclampsia, gestational hypertension, HELLP syndrome, (hemolysis, elevated liver enzymes, low platelets), abruption placenta, chronic hypertension during pregnancy, pregnancy with intra uterine growth restriction, and pregnancy with a small for gestational age (SGA) infant.

"Pre-eclampsia" refers to a multi-system disorder that is characterized by hypertension with proteinuria or edema, or both, glomerular dysfunction, brain edema, liver edema, or coagulation abnormalities due to pregnancy or the influence of a recent pregnancy. All forms of pre-eclampsia, such as premature, mild, moderate, and severe pre-eclampsia are included in this definition. Pre-eclampsia generally occurs after the 20th week of gestation. Pre-eclampsia is generally defined as some combination of the following symptoms: (1) a systolic blood pressure (BP)>140 mm Hg and a diastolic BP>90 mm Hg after 20 weeks gestation (generally measured on two occasions, 4-168 hours apart), (2) new onset proteinuria (1+ by dipstik on urinalysis, >300 mg of protein in a 24-hour urine collection, or a single random urine sample having a protein creatinine ratio>0.3), and (3) resolution of hypertension and proteinuria by 12 weeks postpartum. Severe pre-eclampsia is generally defined as (1) a diastolic BP>110 mm Hg (generally measured on two occasions, 4-168 hours apart) or (2) proteinuria characterized by a measurement of 3.5 grams or more protein in a 24-hour urine collection or two random urine specimens with at least 3+ protein by dipstick. In pre-eclampsia, hypertension and proteinuria generally occur within seven days of each other. In severe pre-eclampsia, severe hypertension, severe proteinuria and HELLP syndrome (hemolysis, elevated liver enzymes, low platelets) or eclampsia can occur simultaneously or only one symptom at a time. HELLP syndrome is characterized by evidence of thrombocytopenia (<100,000 cells/µl), increased LDH (>600 IU/L) and increased AST (>70 IU/L). Occasionally, severe pre-eclampsia can lead to the development of seizures. This severe form of the syndrome is referred to as "eclampsia." Eclampsia can also include dysfunction or damage to several organs or tissues such as the liver (e.g., hepatocellular damage, periportal necrosis) and the central nervous system (e.g., cerebral edema and cerebral hemorrhage). The etiology of the seizures is thought to be secondary to the development of cerebral edema and focal spasm of small blood vessels in the kidney.

"Subject" refers to a mammal, including, but not limited to, a human or non-human mammal such as a cow, a horse, a sheep, a pig, a goat, a dog, or a cat.

"At risk of developing" a pregnancy-related hypertensive disorder such as pre-eclampsia or eclampsia refers to a subject who does not currently have, but has a greater than average chance of developing, a pregnancy-related hypertensive disorder. Such at risk subjects include pregnant women with an sFlt-1 blood concentration of greater than about 3 ng/ml, greater than about 4 ng/ml, greater than about 5 ng/ml, greater than about 6 ng/ml, greater than about 7 ng/ml, greater than about 8 ng/ml, greater than about 9 ng/ml, greater than about 10 ng/ml, greater than about 15 ng/ml, greater than about 20 ng/ml, greater than about 25 ng/ml, greater than about 30 ng/ml, greater than about 40 ng/ml, or greater than about 45 ng/ml, but who show no other signs of a pregnancy-related hypertensive disorder such as pre-eclampsia.

The stage of pregnancy at which the methods described herein may be practiced depends on various clinical factors including the overall health of the subject and the severity of the symptoms of pre-eclampsia. In general, once pre-eclampsia or a predisposition to pre-eclampsia is detected, the methods may be employed. Treatment can be continued for a period of time ranging from 1 to 100 days, more preferably 1 to 60 days, 1 to 10 days, or 1 to 5 days, and most preferably 1 to 20 days.

In certain embodiments, the method is carried out on a subject on or after the 14th week of pregnancy, the 16th week of pregnancy, the 18th week of pregnancy, the 20th week of pregnancy, the 22nd week of pregnancy, the 24th week of pregnancy, the 26th week of pregnancy, the 28th week of pregnancy, the 30th week of pregnancy, the 32nd week of pregnancy, the 34th week of pregnancy, or the 36th week of pregnancy. In certain embodiments, the method is carried out on a subject between the 14th and 16th weeks of pregnancy, the 16th and 18th weeks of pregnancy, the 18th and 20th weeks of pregnancy, the 20th and 22nd weeks of pregnancy, the 22nd and 24th weeks of pregnancy, the 24th and 26th weeks of pregnancy, the 26th and 28th weeks of pregnancy, the 28th and 30th weeks of pregnancy, the 30th and 32nd weeks of pregnancy, the 32nd and 34th weeks of pregnancy, or the 34th and 36th weeks of pregnancy.

In certain embodiments, the subject's blood or plasma is contacted with anti-sFlt-1 antibodies or ligands only to the extent necessary to reduce sFlt-1 to a desired level. A desired level can be, for example, a level of sFlt-1 characteristic of a normal pregnancy. It has been observed that in normal pregnancy, the serum concentration of sFlt-1 decreases from 8-12 weeks to 16-20 weeks, gradually increases at 26-30 weeks, rapidly elevates at 35-39 weeks, and returns to normal level after delivery. Accordingly, in one embodiment, the desired level is the normal level for the subject's stage of pregnancy. In another embodiment, the level is higher or lower that the normal level for the subject's stage of pregnancy. One of ordinary skill in the art would be able to determine a desired level, depending for example on the patient and the frequency with which the ex vivo procedure is to be performed.

The desired sFlt-1 level can be achieved by controlling, for example, the length of time a subject is treated (i.e., the volume of blood or plasma treated for a particular flow rate), the flow rate over the immobilized antibody or ligand, and/or the binding capacity of the solid support bearing the antibody or ligand that binds to sFlt-1. In one embodiment, a diagnostic is used to measure sFlt-1 levels at the time of treatment. In another embodiment, the diagnostic provides a real-time measure of sFlt-1 level and treatment is stopped when the desired sFlt-1 level is reached. In another embodiment, the time, flow rate, and/or capacity is predetermined based on the sFlt-1 level diagnosed in the subject at the start of the procedure and the sFlt-1 level desired to be reached.

In certain embodiments, the method decreases blood levels of sFlt-1 in the subject by 10%-90%, 20%-80%, or 30%-50%, as compared to the blood levels of sFlt-1 in the subject before the method is practiced on the subject. In certain embodiments, the method decreases blood levels of sFlt-1 in the subject by 10%-20%, 20%-30%, 30%-40%, 40%-50%, 50%-60%, 60%-70%, 70%-80%, 80%-90%, or 90%-100% as compared to the blood levels of sFlt-1 in the subject before the method is practiced on the subject.

The anti-sFlt-1 antibodies, or sFlt-1 binding fragments thereof, attached to a solid support, can be used to remove sFlt-1 from the body fluids of subjects suffering from, or at risk of developing, pre-eclampsia or eclampsia. In certain embodiments, the anti-sFlt-1 antibodies, or sFlt-1 binding fragments thereof, attached to a solid support, are used to remove sFlt-1 from blood or blood plasma. In certain embodiments, the anti-sFlt-1 antibodies, or sFlt-1 binding fragments thereof, attached to a solid support are used in extracorporeal immunoadsorbent devices, which are known in the art. Blood or plasma is exposed to the attached support-bound anti-sFlt-1 antibodies, or sFlt-1 binding fragments thereof, resulting in partial or complete removal of circulating sFlt-1 (free or in complexes with other blood proteins), following which the blood or plasma is returned to the subject's body. The methods disclosed herein may be implemented in a continuous flow arrangement, with or without interposing a cell removal step, e.g., a centrifugation step, prior to contact of the blood or plasma with the anti-sFlt-1 antibodies.

Solid supports for use in the methods described herein preferably should be non-toxic and stable when exposed to blood or blood components. The solid supports may be chosen from among those well known in the art. For example, any suitable porous material may be used as the solid support. Examples of suitable solid supports include, e.g., carbohydrate-based materials such as the various types of SEPHAROSE® (a crosslinked, beaded-form of agarose), e.g., SEPHAROSE 4B®, 4FF®, CL-4B® and CL-6B.

The solid support may be comprised of organic or inorganic molecules, or a combination of organic and inorganic molecules, and may be comprised of one or more functional groups, e.g., hydroxyl groups, suitable for forming covalent bonds with activating agents. The solid support may be comprised of a hydrophilic compound, a hydrophobic compound, or any combination thereof. The solid support may be comprised of a polymer or a copolymer.

Examples of suitable materials for use in solid supports include, but are not limited to, agarose, cellulose, polyether sulfones, polyamides, polysaccharides, polytetrafluoroethylene, polyesters, polyurethanes, polyvinylidene fluoride, polypropylene, fluorocarbons, e.g., poly(tetrafluoroethylene-co-perfluoro(alkyl vinyl ether)), polyethylene, glass, polycarbonates, polyacrylate, polyacrylamide, poly(azolactone), polystyrene, ceramics, and nylon.

The solid support need not be in any particular shape. For example, the solid support may be in the form of beads, membranes, gels, columns, chips, plates, tubes, sheets, fibers, or hollow fibers. The solid support can also be in the form of a coating on the interior of one or more lengths of tubing, piping, or hollow fibers through which blood or plasma flows. In such embodiments, the tubing, piping, or hollow fibers are preferably coiled or otherwise convoluted or bent, in order to maximize the amount of solid support contacted by the blood or plasma flowing through the tubing, piping, or hollow fibers.

Methods of attaching antibodies and ligands to a solid support are well known in the art and may be used to attach the anti-sFlt-1 antibodies, or sFlt-1 binding fragments thereof, used in the methods described herein to a solid support. Such methods include, without limitation, the use of cyanogen bromide, 1,1'-carbonyldiimidazole (CDI), or triethylamine.

In general, solid supports may be activated for the attachment of anti-sFlt-1 antibodies, or sFlt-1 binding fragments thereof, by contacting the solid supports with an activating agent such as an aldehyde, an epoxide, a cyanogen, or an activated carboxylic acid.

Methods of attaching antibodies to solid supports are well known in the art. See, e.g., Hermanson et al. 1992, Immobilized Affinity Ligand Techniques, Academic Press; U.S. Pat. No. 5,874,165; U.S. Pat. No. 3,932,557; U.S. Pat. No. 4,772,635; U.S. Pat. No. 4,210,723; U.S. Pat. No. 52,506,123; European Patent Application EP 1 352 957 A1, and International Patent Publication WO 2004/074471. Typically, the solid support is activated with a reactive functional group such as an epoxide (e.g., by the use of epichlorohydrin), cyanogens (e.g., cyanogen bromide (CNBr)), N,N-disuccinimidylcarbonate (DSC), aldehydes, or an activated carboxylic acid (e.g., N-hydroxysuccinimide (NHS) esters, or carbonyldiimidazole (CDI) activated esters). Activated groups may be attached directly to the solid support, as is generally the case for CNBr, or the activated groups may be part of a linker or spacer molecule, which is typically a linear chain of carbon, optionally substituted with oxygen and/or nitrogen atoms. A typical example of such a linker is the ten membered chain of carbon and oxygen found in the linker butanediol digycidyl ether (a common epoxide coupling agent). The activated solid support is then contacted with the antibody under coupling conditions.

Other linkers may include a branched, unbranched, or cyclic carbon chain comprising from 1 to 30 carbon atoms. In certain embodiments, the linker may be comprised of more than 30 carbon atoms. The linker may comprise at least one hetero-atom such as nitrogen, oxygen, or sulfur.

The commercial product AFFI-GEL 150 (BioRad, Hercules, Calif.) may be used for linker-assisted coupling. AFFI-GEL 150 is an agarose support derivatized with an NHS activated carboxylic acid as part of a linker arm containing a positively charged secondary amine. Another charged linker is disclosed in U.S. Pat. No. 5,260,373. A shorter linker arm comprised of arginine may be used to facilitate coupling to an agarose support. The arginine linker is activated with NHS and carries a positive charge.

Anti-sFlt-1 antibodies, binding fragments thereof, and sFlt-1 specific polypeptides and ligands can be covalently coupled to a solid support in a manner that provides more uniform orientation and efficient sFlt-1 binding. Most methods involve modifying a protein with a unique chemical group at a predefined position, and reacting that group with a complementary group on the solid support. In another embodiment, anti-sFlt-1 antibodies, antibody fragments, and ligands are produced with N- or C-terminal linkers capable of being coupled to a solid support. In certain embodiments, polypeptides and ligands are synthesized directly on a solid support.

Diagnostic methods known in the art can be used to monitor a subject's pre-eclampsia or eclampsia during therapy to determine the effectiveness of therapy according to the methods disclosed herein. Suitable diagnostic methods are disclosed in, e.g., U.S. Pat. No. 7,335,362; U.S. Pat. No. 7,435,419; and U.S. Pat. No. 7,407,659.

In certain embodiments, diagnostic methods are employed that determine and/or monitor the concentration of sFlt-1 in a subject's blood in order to identify subjects suitable for treatment or prevention using the methods disclosed herein. In certain embodiments, diagnostic methods are employed to identify subjects at risk of developing a pregnancy-related hypertensive disorder such as pre-eclampsia or eclampsia where the subjects are pregnant women with an sFlt-1 blood concentration of greater than about 5 ng/ml, greater than about 6 ng/ml, greater than about 7 ng/ml, greater than about 8 ng/ml, greater than about 9 ng/ml, greater than about 10 ng/ml, greater than about 15 ng/ml, greater than about 20 ng/ml, greater than about 25 ng/ml, greater than about 30 ng/ml, greater than about 40 ng/ml, or greater than about 45 ng/ml, but who show no other signs of a pregnancy-related hypertensive disorder such as pre-eclampsia.

Accordingly, the present invention provides a method of identifying a subject having, or at risk of developing, a pregnancy-related hypertensive disorder and then practicing the ex vivo methods disclosed herein on the subject so identified, thereby treating or preventing the pregnancy-related hypertensive disorder. In certain embodiments, a pregnant human is identified as a subject suitable for treatment or prevention by the methods disclosed herein if the concentration of sFlt-1 in the subject's blood during the second trimester of pregnancy is determined to be above about 3.5 ng/ml, above about 4 ng/ml, above about 5 ng/ml, above about 7.5 ng/ml, above about 10 ng/ml, above about 20 ng/ml, above about 30 ng/ml, above about 40 ng/ml, or above about 50 ng/ml.

In certain embodiments where the subject's blood levels of sFlt-1 are determined and/or monitored, the methods described herein may be employed until the concentration of sFlt-1 in the subject's blood is less than about 50 ng/ml, less than about 45 ng/ml, less than about 40 ng/ml, less than about 35 ng/ml, less than about 30 ng/ml, less than about 25 ng/ml, less than about 20 ng/ml, less than about 15 ng/ml, less than about 10 ng/ml, less than about 7.5 ng/ml, less than about 5 ng/ml, less than about 4 ng/ml, less than about 3 ng/ml, less than about 2 ng/ml, less than about 1.5 ng/ml, or less than about 1 ng/ml.

In certain embodiments, the methods disclosed herein may be employed until an improvement is detected in the symptoms of a pregnancy-related hypertensive disorder. In certain embodiments, the pregnancy-related hypertensive disorder is pre-eclampsia and the improvement is a decrease in blood pressure to a value of less than 140 mmHg (systolic) and/or less than 90 mmHg (diastolic).

The present invention provides a housing or chamber such as a column containing anti-sFlt-1 antibodies, or sFlt-1 binding fragments thereof, bound to a solid support, where the housing or chamber is suitable for use in treating or preventing a pregnancy-related hypertensive disorder such as eclampsia or pre-eclampsia.

In certain embodiments, the housing or chamber is a column. "Column" refers to a container, chamber, or housing, generally cylindrical in shape, containing a solid support to which anti-sFlt-1 antibodies, or sFlt-1 binding fragments thereof, or sFlt-1 ligands, can be or have been attached.

In certain embodiments, the column contains a volume of about 5 ml to 2000 ml, about 10 ml to about 1000 ml, about 50 ml to about 500 ml, or about 200 ml to about 400 ml of anti-sFlt-1 antibodies, or sFlt-1 binding fragments thereof, bound to a solid support. In certain embodiments, the column contains a volume of about 5 ml, about 10 ml, about 25 ml, about 50 ml, about 100 ml, about 200 ml, about 300 ml, about 500 ml, about 750 ml, about 1000 ml, about 1500 ml, or about 2000 ml of anti-sFlt-1 antibodies, or sFlt-1 binding fragments thereof, bound to a solid support. In certain embodiments, the column contains one or more anti-coagulant substances, e.g., heparin. In certain embodiments, the interior of the column has been treated in a manner intended to reduce the amount of bacteria, mycoplasma and/or viruses in the interior of the column. In certain embodiments, the interior of the column is sterile.

In certain embodiments, the column contains sufficient anti-sFlt-1 antibodies, or sFlt-1 binding fragments thereof, bound to a solid support, to remove at least 10 µg, at least 25 µg, at least 50 µg, at least 75 µg, at least 100 µg, at least 150 µg, at least 200 µg, at least 300 µg, at least 400 µg, at least 500 µg, at least 600 µg, at least 700 µg, at least 800 µg, at least 900 µg, at least 1000 µg, at least 1500 µg, or at least 2000 µg of sFlt-1 from human blood or plasma. In certain embodiments, the column contains sufficient anti-sFlt-1 antibodies, or sFlt-1 binding fragments thereof, bound to a solid support, to remove at least 10 µg to 2000 µg, at least 20 µg to 1000 µg, at least 50 µg to 500 µg, or at least 100 µg to 200 µg of sFlt-1 from human blood or plasma.

The present invention provides methods of making a device for treating or preventing a pregnancy-related hypertensive disorder such as eclampsia or pre-eclampsia comprising:

(a) attaching anti-sFlt-1 antibodies, or sFlt-1 binding fragments thereof, to a solid support to produce anti-sFlt-1 antibodies, or sFlt-1 binding fragments thereof, bound to a solid support, (b) introducing the anti-sFlt-1 antibodies, or sFlt-1 binding fragments thereof, bound to the solid support into a housing or chamber such as a column to produce a housing or chamber containing the anti-sFlt-1 antibodies, or sFlt-1 binding fragments thereof, bound to the solid support, (c) fluidly connecting the housing or chamber containing the anti-sFlt-1 antibodies, or sFlt-1 binding fragments thereof, bound to the solid support, to a means for conveying blood or plasma from a subject to the anti-sFlt-1 antibodies, or anti-sFlt-1 antigen binding fragments thereof, bound to the solid support, (d) fluidly connecting the housing or chamber containing the anti-sFlt-1 antibodies, or sFlt-1 binding fragments thereof, bound to the solid support, to a means for conveying the blood or plasma from the anti-sFlt-1 antibodies, or sFlt-1 binding fragments thereof, bound to the solid support, to the subject, where the means are connected to the housing or chamber so as to allow for contact of the blood or plasma from the subject with the anti-sFlt-1 antibodies, or anti-sFlt-1 antigen binding fragments thereof, bound to the solid support, and thereby remove sFlt-1 from the blood or plasma.

The present invention provides methods of making a device for treating or preventing a pregnancy-related hypertensive disorder such as eclampsia or pre-eclampsia comprising modifying a dialysis or apheresis device or system so as to provide the dialysis or apheresis device or system with a housing or chamber such as a column containing anti-sFlt-1 antibodies, or sFlt-1 binding fragments thereof, bound to a solid support, so as to allow the dialysis or apheresis device or system to provide for the contact of blood or plasma from a subject with the anti-sFlt-1 antibodies, or anti-sFlt-1 antigen binding fragments thereof, bound to the solid support, and thereby remove sFlt-1 from the blood or plasma to produce sFlt-1-depleted blood or plasma.

In certain embodiments, the present invention provides methods of identifying an anti-sFlt-1 antibody suitable for use in ex vivo methods of treating or preventing a pregnancy-related hypertensive disorder such as eclampsia or pre-eclampsia comprising:

(a) obtaining an antibody that binds to sFlt-1;

(b) attaching the antibody that binds to sFlt-1 to a solid support to produce a solid support comprising bound anti-sFlt-1 antibody;

(c) determining if the solid support comprising bound anti-sFlt-1 antibody can bind sFlt-1 in a fluid sample from a subject and thereby remove sFlt-1 from the fluid sample;

where if the solid support comprising bound anti-sFlt-1 antibody can bind sFlt-1 in a fluid sample from a subject and thereby remove sFlt-1 from the fluid sample, the antibody of step (a) is identified as an anti-sFlt-1 antibody suitable for use in ex vivo methods of treating or preventing a pregnancy-related hypertensive disorder such as eclampsia or pre-eclampsia.

In certain embodiments, the subject is a mammal. In certain embodiments, the subject is a human.

In certain embodiments, the fluid sample is blood, plasma, amniotic fluid, or urine.

A modified dialysis or apheresis system can be used to practice the methods disclosed herein, wherein the modified dialysis or apheresis system provides the means by which blood is removed, passed over a solid support containing bound anti-sFlt-1 antibodies, or sFlt-1 binding fragments thereof, and returned to the subject's body following removal of sFlt-1 from the blood by the anti-sFlt-1 antibodies, or sFlt-1 binding fragments thereof. In some embodiments, the apheresis system is a plasmapheresis system and plasma rather than blood is passed over a solid support containing bound anti-sFlt-1 antibodies, or sFlt-1 binding fragments thereof, and returned to the subject's body following removal of sFlt-1 from the plasma by the anti-sFlt-1 antibodies, or sFlt-1 binding fragments thereof.

In certain embodiments, the methods disclosed herein may be carried out using a modified version of a device known in the art that enables removal and extracorporeal treatment of a body fluid such as whole blood or plasma. One such device is a dialysis machine. Dialysis machines are in routine use and methods to control blood flow, remove air bubbles, and maintain proper electrolyte balance, blood sugar, oxygenation, temperature, sterility, and other vital factors during dialysis, are well known and established in the art. In certain embodiments, the methods disclosed herein may be carried out using existing dialysis systems where the dialyzer is replaced by a housing or chamber, such as a column, containing a solid support to which anti-sFlt-1 antibodies, or sFlt-1 binding fragments thereof, are attached. When blood flows through the housing or chamber, the anti-sFlt-1 antibodies, or sFlt-1 binding fragments thereof, remove sFlt-1 from the blood, thereby lowering the concentration of sFlt-1 in the blood and treating or preventing a pregnancy-related hypertensive disorder such as pre-eclampsia or eclampsia.

Another well known device that can be used to practice the methods described herein is an apheresis system, e.g., a plasmapheresis system. Plasmapheresis involves the extracorporeal manipulation and removal of certain cellular components of the blood, after which the blood is reinfused into the subject to induce a desired clinical effect. During plasmapheresis, blood is initially taken out of the body through an access device such as a needle or catheter. Plasma is then removed from the blood by a cell separator. Three procedures are commonly used to separate the plasma from blood cells: (1) Discontinuous flow centrifugation, where, typically, a 300 ml volume of blood is removed at a time and centrifuged to separate plasma from blood cells. (2) Continuous flow centrifugation, where centrifugation is used to continuously spin out plasma. (3) Plasma filtration, where the plasma is filtered using standard hemodialysis equipment.

Apheresis devices suitable for modification for use in the methods disclosed herein are described, e.g., in U.S. Pat. No. 5,098,372; U.S. Pat. No. 5,112,298; and U.S. Pat. No. 6,319,471. Other suitable devices include the LIFE-18® plasma therapy device from PlasmaSelect (Munich, Germany), the Diapact® CRRT from B. Braun (Melsungen, Germany), the COBE SPECTRA®, a product of Cobe BCT, Incorporated, 1201 Oak Street, Lakewood, Co. 80215, and the ELUTRA® Cell Separation System of Gambro BCT, Inc.

In certain embodiments of the systems disclosed herein, the access device for accessing a subject's blood system and/or the return device for returning blood, plasma, or cellular components of blood to a subject is a single lumen catheter or a double lumen catheter such as, e.g., the single lumen or double lumen catheters sold by Fresenius Medical Care (Bad Homburg, Germany). Such catheters may be made of thermosensitive polyurethane that adapts to the contour of a blood vessel as the polyurethane heats to body temperature.

In certain embodiments of the methods disclosed herein, removing blood from the subject includes removing an amount of blood from the subject sufficient to derive at least about 650 milliliters of plasma from the blood. In certain embodiments, removing the blood from the subject includes removing at least two liters of blood from the subject. In certain embodiments, removing the blood from the subject includes continuously removing blood from the subject until substantially the entire blood volume of the subject is contacted with anti-sFlt-1 antibodies, or sFlt-1 binding fragments thereof, at least once, at least twice, or at least three times. In certain embodiments, removing the blood from the subject includes continuously removing blood from the subject until about two-thirds, about half, about one-fourth, about one-fifth, or about one-tenth of the entire blood volume of the subject is contacted with anti-sFlt-1 antibodies, or sFlt-1 binding fragments thereof. In certain embodiments, removing the blood from the subject includes continuously removing blood from the subject until the concentration of sFlt-1 in the subject's blood reaches a preselected concentration. In certain embodiments, the preselected concentration is less than about 50 ng/ml, less than about 40 ng/ml, less than about 25 ng/ml, less than about 10 ng/ml, less than about 5 ng/ml, less than about 4 ng/ml, less than about 3 ng/ml, less than about 2 ng/ml, less than about 1 ng/ml, less than about 0.75 ng/ml, or less than about 0.5 ng/ml. In certain embodiments, the preselected concentration is about 40-50 ng/ml, about 30-40 ng/ml, about 20-30 ng/ml, about 10-20 ng/ml, about 5-10 ng/ml, about 5-8 ng/ml, about 3-7 ng/ml, about 1-5 ng/ml, about 1-3 ng/ml, about 0.75-2 ng/ml, or about 0.5-1 ng/ml.

The sFlt-1 concentration can be measured automatically in blood or plasma, either continuously, or at preset intervals. For example, plasma samples from the subject can be reacted with a labeled reagent that binds to sFlt-1 or particles containing sFlt-1 and the amount of sFlt-1 measures. Alternatively, a sensor with a linked reagent that specifically binds to sFlt-1 (including particles containing sFlt-1) can be used to continuously detect the amount of bound sFlt-1. The blood filtration procedure is terminated when the concentration of sFlt-1 detected in a subject's blood or plasma drops below a predetermined value.

EXAMPLES

Example 1

Removal of sFlt-1 from Human Amniotic Fluid Using a Column Device Containing a Solid Support with Bound Anti-sFlt-1 Antibodies or Ligands The experimental conditions were designed to approximate use in a clinical setting, but on a smaller scale. Amniotic fluid was obtained from human pre-eclampsia patients with elevated sFlt-1 levels of about 40 ng/ml.

All of the antibodies used were mouse monoclonal antibodies which bind to sFlt-1, with the exception of one control column which used polyclonal antibodies to human Factor VIII. The anti-sFlt-1 monoclonal antibodies were made by immunizing mice with human sFlt-1 protein (Ig-like domains 1-3) which includes amino acids Ser27 to Ile328. This protein also had a poly-histidine affinity tag at the carboxy terminal. 12 antibodies that bound to sFlt-1 were selected and tested for binding affinity to sFlt-1.

A device for removing sFlt-1 protein from a biological solution was made by attaching anti-sFlt-1 antibodies to a solid phase matrix (agarose beads). The agarose beads were chemically treated with cyanogen bromide to create a reactive chemical group on the beads. These activated beads were then mixed with antibody to covalently attach the antibodies to the beads.

The beads with attached antibodies were then poured into a 1 ml column containing a screen/frit at the bottom, retaining the beads inside the column, but allowing fluids or solutions to pass through the column. To the resulting device, containing anti-sFlt-1 antibodies attached to beads, amniotic fluid from pre-eclampsia patients was added at the top of the device and the solution that flowed through the device and out the bottom of the column was collected. The amount of sFlt-1 in the amniotic fluid before and after passing through the device was measured, and the % of depleted sFlt-1 was calculated.

Further details were as follows:

(1) 0.1 ml of agarose beads coupled to anti-sFlt-1 antibody were added to a 1 ml column.

(2) 500 µg of antibody were bound to the agarose beads.

(3) The column was washed with 4 ml of phosphate buffered saline (PBS).

(4) 1 ml of amniotic fluid from pre-eclampsia patients (containing approximately 40 ng of sFlt-1 protein) was added to the top of the column.

(5) The amniotic fluid was run over the column at a flow rate of approximately 1 ml/15 min. at room temperature (21-24° C.).

(6) The amniotic fluid was collected and re-applied to the device two times, resulting in a total of three passages over the column.

(7) After the third passage over the column, the flow-through solution was collected and tested for sFlt-1 concentration.

(8) The device was washed with 4 ml of buffer to remove any material that bound non-specifically to the beads/column. Then 0.5 ml of 0.5 M acetic acid (pH 3.0) was added to the device to disassociate the bound sFlt-1 from the device. The fractions of the eluted solution were collected and the sFlt-1 concentration was measured to determine whether there was any change.

Results for exemplary antibodies, including affinity for sFlt-1 and % sFlt-1 removed from amniotic fluid are shown in Table 2 below.

TABLE 2

| Sample | Kd (M) | % sFlt-1 removed |
|---|---|---|
| amniotic fluid before column | | 0 |
| column (no antibody) | | 0 |
| column with Factor VIII antibody | | <1 |
| column with antibody 101 | 1.44E−09 | 53 |
| column with antibody 102 | 2.17E−10 | 85 |
| column with antibody 103 | 3.12E−10 | 87 |
| column with antibody 104 | n.d. | 85 |
| column with antibody 105 | 7.05E−08 | <1 |
| column with antibody 106 | 1.58E−09 | 59 |
| column with antibody 107 | 8.11E−09 | <1 |
| column with antibody 108 | 4.99E−09 | 11 |
| column with antibody 109 | 7.66E−10 | 48 |
| column with antibody 110 | 3.36E−10 | 58 |
| column with antibody 111 | 3.18E−10 | 50 |
| column with antibody 112 | 5.35E−10 | 28 |
| column with $VEGF_{121}$ | n.d. | 50 |

A similar method was used with $VEGF_{121}$. $VEGF_{121}$ was expressed in bacteria, purified by column chromatography, and coupled to cyanogen bromide-activated agarose beads. Otherwise, the procedure for applying amniotic fluid to the column containing the agarose bead-coupled VEGF$_{121}$ was substantially the same as for the antibodies.

Figure 2:
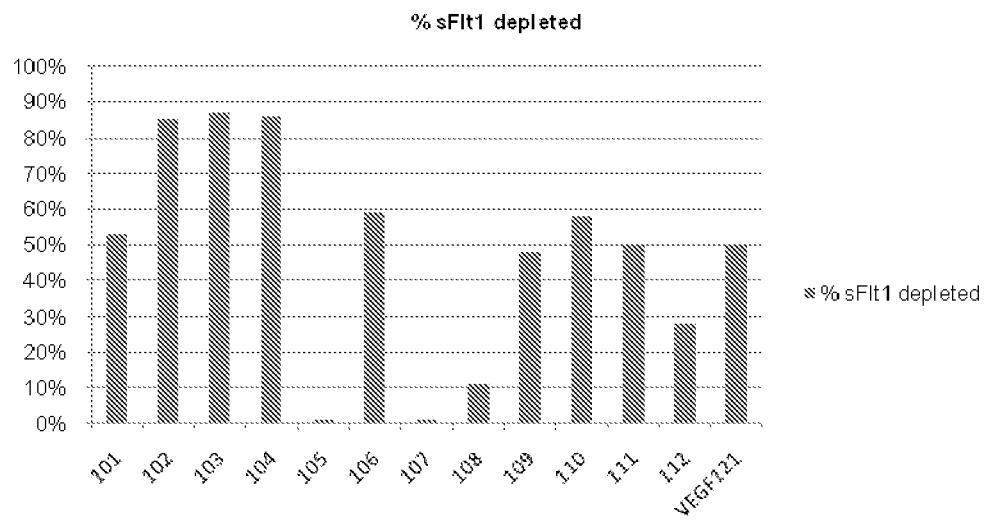
FIG. 2 illustrates the depletion of sFlt-1 from a solution comprising sFlt-1 by the use of sFlt-1 binding compounds, including anti-sFlt-1 antibodies and $VEGF_{121}$ bound to a solid support (panel A) and apparent $K_d$ measurements of purified monoclonal antibodies and Flt-1 by ForteBio Octet (panel B).
Figure 2:
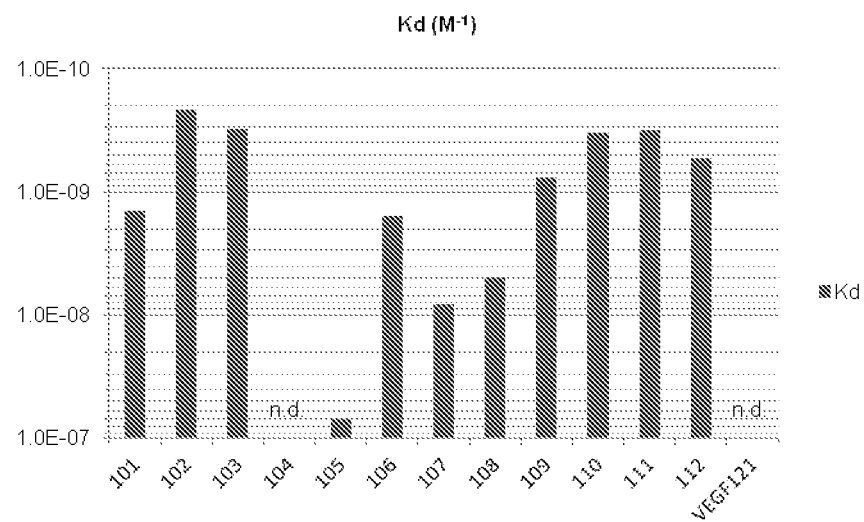
Figure 3:
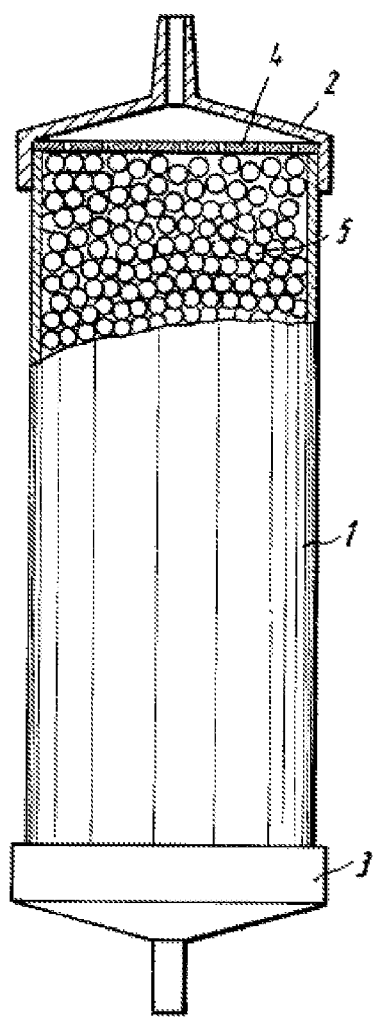
FIG. 3 shows one embodiment of a column comprising anti-sFlt-1 antibodies, or anti-sFlt-1 antigen binding fragments thereof, bound to a solid support. The column comprises a cylindrical housing 1 and two connecting caps 2 and 3, where cap 2 is connected to a means for delivering blood or plasma from a subject to the anti-sFlt-1 antibodies, or sFlt-1 antigen binding fragments thereof, bound to the solid support, and cap 3 is connected to a means for returning the sFlt-1-depleted blood or plasma to the subject following contact of the blood or plasma with the anti-sFlt-1 antibodies, or sFlt-1 antigen binding fragments thereof, bound to the solid support. Upper disk 4 is a barrier inserted into cap 2 which keeps the solid support 5 away from the inlet opening. A similar disk is present in lower cap 3 but is not shown. Solid support 5 is depicted here in the form of beads, but may be any convenient shape. The anti-sFlt-1 antibodies are not shown, but are bound to solid support 5. 1, 2, 3, and 4 are made of blood compatible synthetic materials and are interconnected by conventional techniques.

The results for the anti-sFlt-1 antibodies and VEGF$_{121}$ are shown in FIG. 2.

The results show that anti-sFlt-1 antibodies and sFlt-1 ligand bound to a solid support were able to specifically remove sFlt-1 from amniotic fluid of pre-eclamptic patients. A control column device containing the matrix/beads only with no antibody or ligand attached did not remove sFlt-1 protein from amniotic fluid. A control column device containing an antibody that binds to coagulation Factor VIII also did not remove sFlt-1. However, when antibodies or ligands that bind sFlt-1 were used in the column, sFlt-1 protein levels were reduced in the flow-through amniotic fluid by up to 87%. A significant variation in how effective individual antibodies were in removing sFlt-1 was observed (11-87%). The apparent Kd of binding between purified monoclonal antibodies and sFlt1 was measured by surface plasmon resonance (SPR). (FIG. 2B). Antibodies were immobilized on the solid phase and sFlt-1 (domains 1-3) was in the liquid phase. There was no direct correlation between antibody affinity (as measured in a kinetic binding experiment) (FIG. 2B) and effectiveness (FIG. 2A) in the device. There was also no direct correlation with on-rates or off-rates and device effectiveness. These results show that devices comprising anti-sFlt-1 antibodies bound to a solid support can be used to treat pregnancy-related hypertensive disorders, including pre-eclampsia.

Example 2

Chimerization

Chimeric monoclonal antibodies were produced having murine variable regions and human IgG1 constant regions. Several variations of chimeric antibody were produced. Antibody AG10A (V$_H$: SEQ ID NO:35; V$_L$: SEQ ID NO:36) consists of the heavy and light chain variable domains of antibody 102 and a human IgG1 constant region. Antibody AG10B (V$_H$: SEQ ID NO:37; V$_L$: SEQ ID NO:36) incorporates a mutation (N298Q) that removes a glycosylation site in the constant region. Antibody AG10C (V$_H$: SEQ ID NO:38; V$_L$: SEQ ID NO:36) incorporates a mutation (I254A) that disrupts binding to FcRn. Antibody AG10D (V$_H$: SEQ ID NO:39; V$_L$: SEQ ID NO:36) incorporates both of the aforementioned mutations.

Example 3

Characteristics of Immobilized Antibody AG10B

Various tests of the sFlt-1 depletion characteristics of Antibody AG10B were performed.

Figure 4:
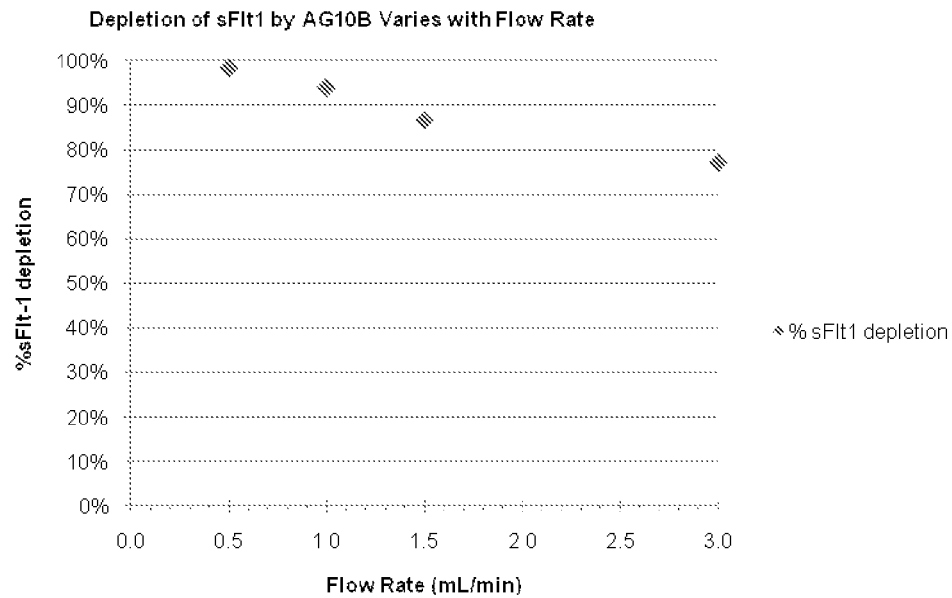
FIG. 4 shows the effect of flow rate on sFlt-1 depletion by antibody AG10B.

Flow Rate—Forty bed volumes of horse serum spiked with 40 ng/mL of sFlt1 (Input) was applied to a column containing 1 mL of packed Sepharose beads coupled to AG10B monoclonal antibody (0.8 mg), and the flow-through fractions (FT) were collected. The sFlt1 concentrations in the Input and FT fractions were determined using the R&D Flt-1 DuoSet kit (DY321). The % sFlt1 depletion was calculated by the formula, % sFlt1 depletion=[(sFlt1$_{Input}$−sFlt1$_{FT}$)/sFlt1$_{Input}$]. The variation of sFlt-1 depletion with flow rate is shown in Table 3 and FIG. 4.

TABLE 3

| Flow Rate (mL/min) | % sFlt1 depletion |
| --- | --- |
| 0.5 | 98% |
| 1.0 | 94% |
| 1.5 | 87% |
| 3.0 | 77% |

Figure 5:
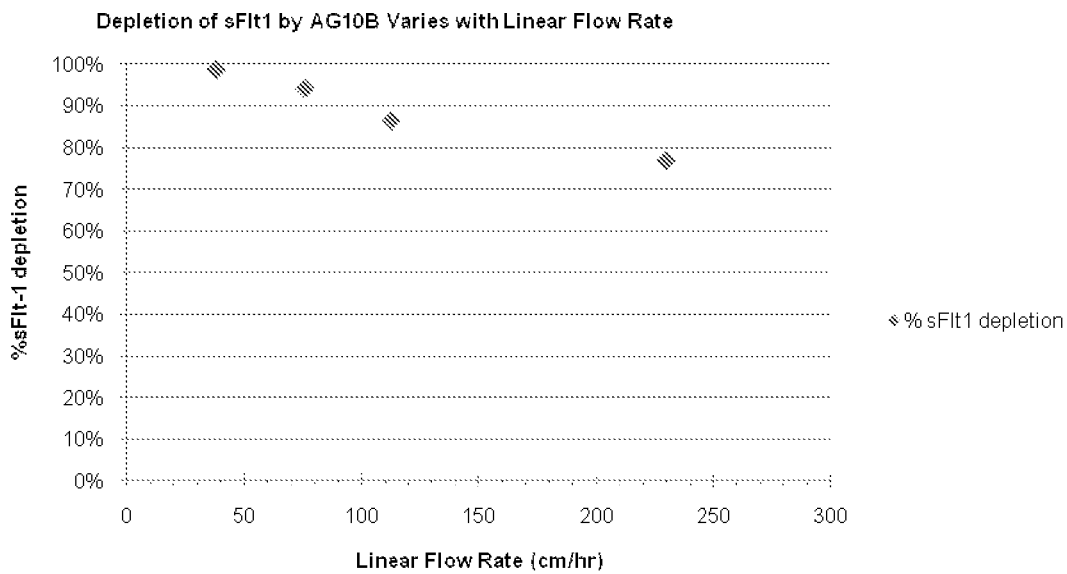
FIG. 5 shows the effect of linear flow rate on sFlt-1 depletion by antibody AG10B.

Linear Flow Rate—Forty bed volumes of horse serum spiked with 40 ng/mL of sFlt1 (Input) was applied to a column containing 1 mL of Sepharose beads coupled to AG10B monoclonal antibody (0.8 mg), and the flow-through fractions (FT) were collected. The sFlt1 concentrations in the Input and FT fractions were determined using the R&D Flt-1 DuoSet kit (DY321). The % sFlt1 depletion was calculated by the formula, % sFlt1 depletion=[(sFlt1$_{Input}$−sFlt1$_{FT}$)/sFlt1$_{Input}$]. The variation of sFlt-1 depletion with linear flow rate is shown in Table 4 and FIG. 5.

TABLE 4

| Linear Flow Rate (cm/hr) | % sFlt1 depletion |
| --- | --- |
| 38 | 98% |
| 76 | 94% |
| 113 | 87% |
| 230 | 77% |

Figure 6:
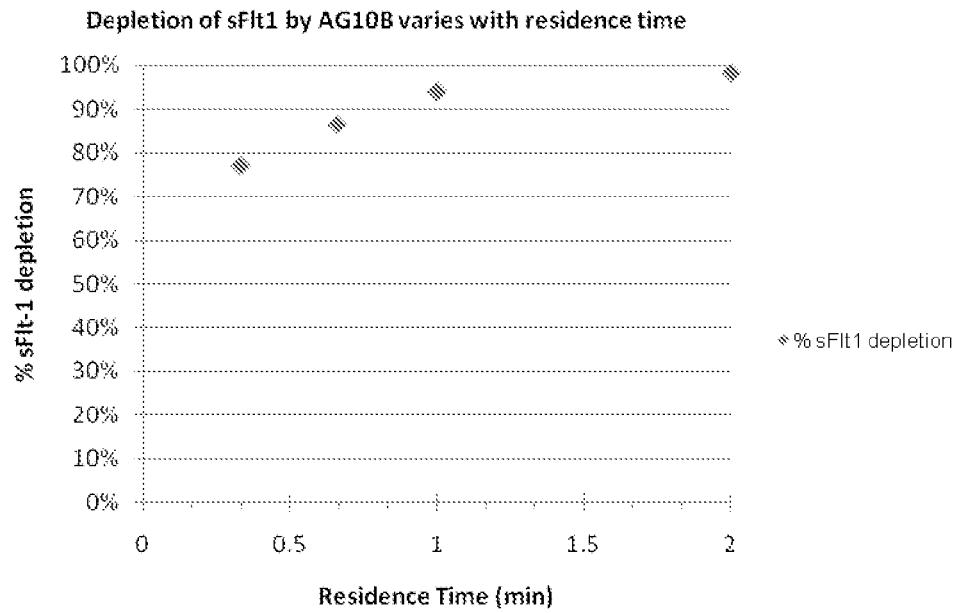
FIG. 6 shows the effect of residence time on sFlt-1 depletion by antibody AG10B.

Residence Time—Forty bed volumes of horse serum spiked with 40 ng/mL of sFlt1 (Input) was applied to a column containing 1 mL of Sepharose beads coupled to AG10B monoclonal antibody (0.8 mg), and the flow-through fractions (FT) were collected. The sFlt1 concentrations in the Input and FT fractions were determined using the R&D Flt-1 DuoSet kit (DY321). The % sFlt1 depletion was calculated by the formula, % sFlt1 depletion=[(sFlt1$_{Input}$−sFlt1$_{FT}$)/sFlt1$_{Input}$]. The variation of sFlt-1 depletion with column residence time is shown in Table 5 and FIG. 6.

TABLE 5

| Residence Time (min) | % sFlt1 depletion |
| --- | --- |
| 0.33 | 77% |
| 0.67 | 87% |
| 1.00 | 94% |
| 2.00 | 98% |

Monoclonal Ab Density—Horse serum spiked with recombinant sFlt1 was applied over a 1-mL column containing Sepharose beads (about 1.5×10$^6$ beads/ml), coupled to various amounts of AG10B at flow rate of 0.5 mL/min (residence time of 2 min).

Figure 7:
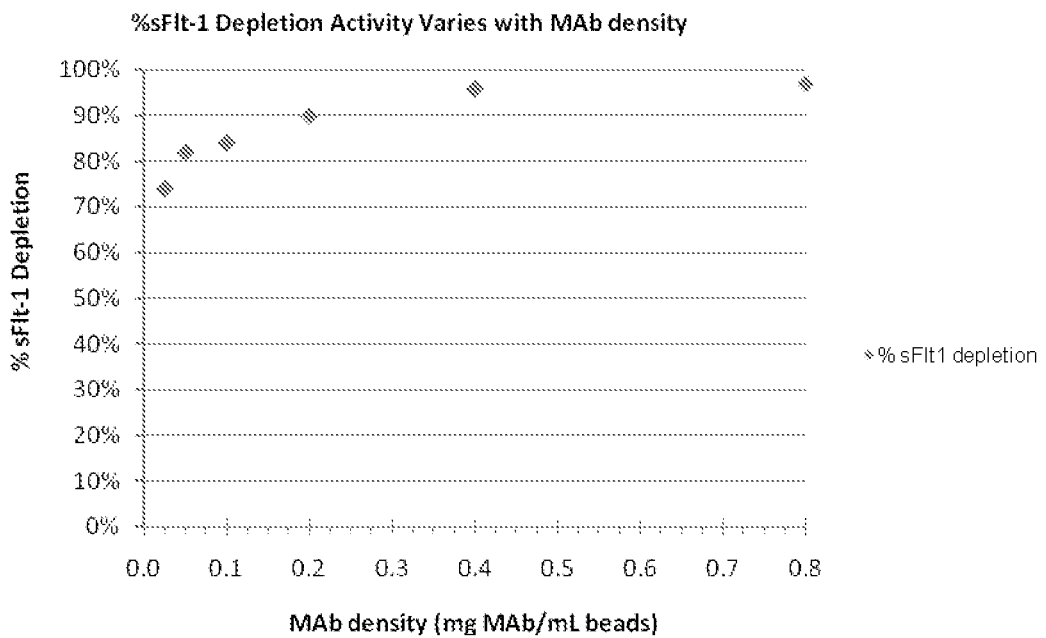
FIG. 7 shows the effect of AG10B density on sFlt-1 depletion.

For 0.8 mg of Ab (about 3.2×10$^{15}$ molecules) per ml, this amounts to about 2.1×10$^9$ molecules per bead. Similarly, at 0.4 mg of Ab (1.6×10$^{15}$ molecules) there are about 1.05×10$^9$ moleculesper bead. Given a bead surface area of 2.5×10$^{-4}$ cm$^2$, 0.8 mg of Ab per 1 mL beads amounts to about 8.4×E$^{12}$ Ab molecules per cm$^2$ bead surface area (not including pores). The % sFlt1 depletion was determined by dividing the depleted amount of sFlt1 by the total sFlt1 input. The sFlt1 concentrations were determined using the R&D Flt-1 DuoSet kit (DY321). The variation of sFlt-1 depletion with MAb density is shown in Table 6 and FIG. 7.

TABLE 6

| Ab density (mg/mL beads) | % sFlt1 depletion |
|---|---|
| 0.025 | 74% |
| 0.050 | 82% |
| 0.100 | 84% |
| 0.200 | 90% |
| 0.400 | 96% |
| 0.800 | 97% |

Depletion of sFlt-1 from plasma and serum.

Figure 8:
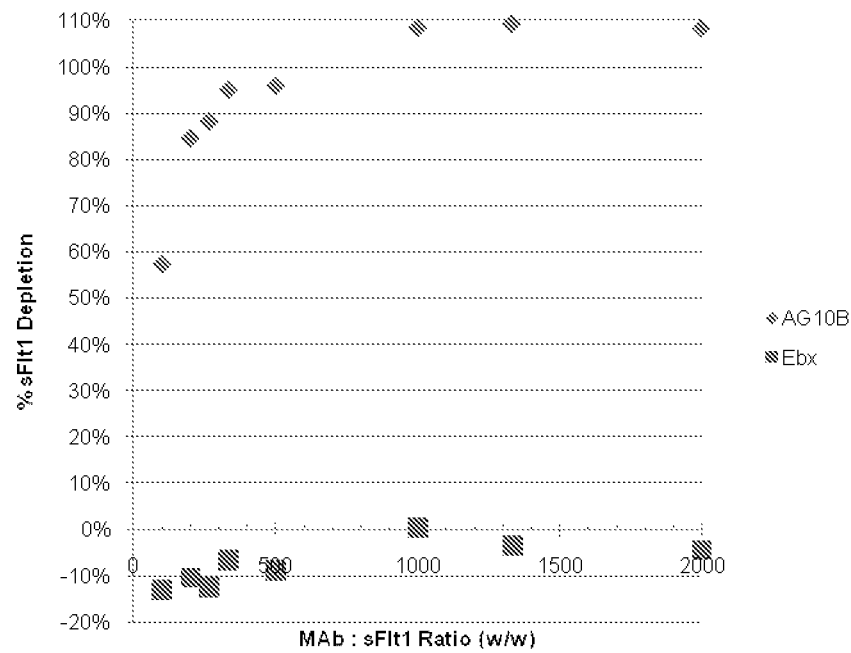
FIG. 8 shows depletion of sFlt-1 from plasma over a range of AG10B:sFlt-1 ratios. A non-specific antibody, Erbitux, does not deplete sFlt-1, indicating that the effect of AG10B is specific.

Normal human plasma spiked with recombinant sFlt1 was applied over 0.1-mL columns containing Sepharose beads coupled to AG10B or Erbitux. The percent of depletion was determined for a wide range of Ab:ligand ratios. Diminished capacity of the column occurs when the AG10B:sFlt1 ratio is below 200:1. (FIG. 8). Column runs were performed by gravity flow so residence time and flow rates were variable. Amounts of sFlt1 were determined by R&D Flt-1 DuoSet kit (DY321).

Figure 9:
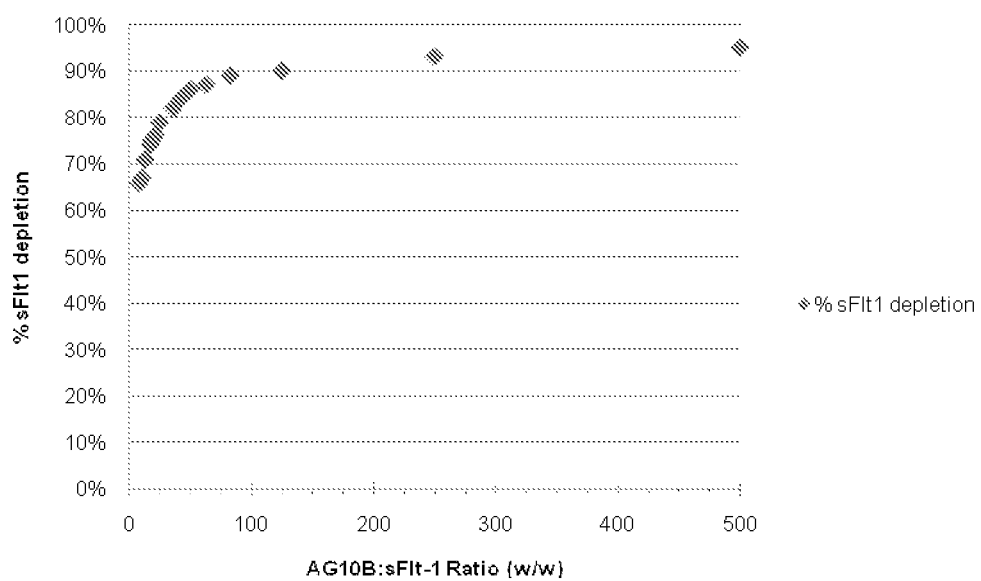
FIG. 9 shows depletion of sFlt-1 from serum over a range of AG10B:sFlt-1 ratios.
Figure 10:
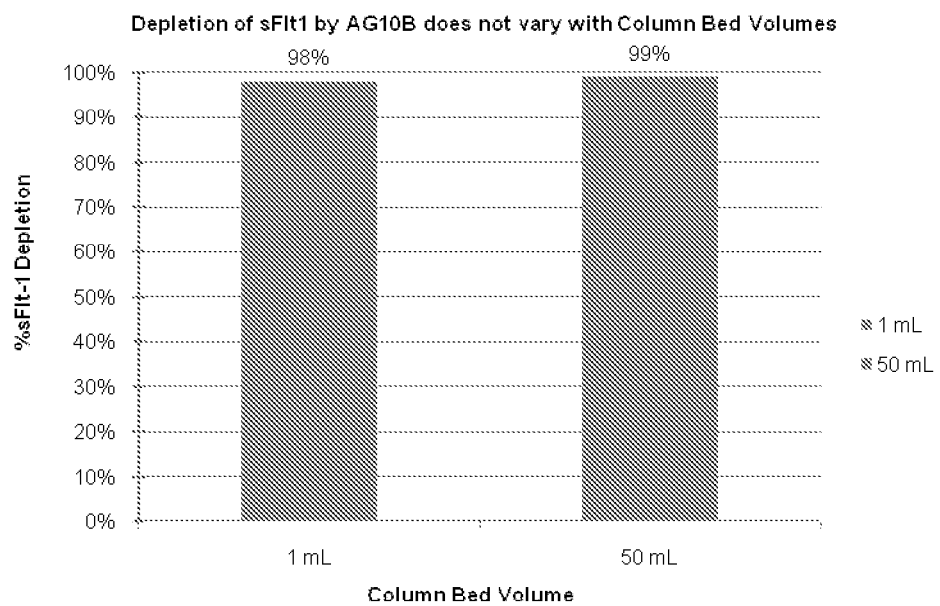
FIG. 10 shows depletion of sFlt-1 is not affected by column bed volume.

Horse serum spiked with recombinant sFlt1 was applied over 1-mL columns containing Sepharose beads coupled to AG10B. The percent of depletion was determined for range of MAb:ligand ratios. Diminished capacity of the column occurs when the AG10B:sFlt1 ratio is below 25:1. (FIG. 9). Columns were run at 1 mL/min with a residence time of 1 min. Amounts of sFlt1 were determined by R&D Flt-1 DuoSet kit (DY321).

sFlt-1 depletion by AG10B does not vary with column size. Horse serum spiked with 40 bed volumes of 40 ng/mL of sFlt1 was applied at residence time of 2 min to either 1-mL or 50-mL columns containing Sepharose beads coupled to AG10B monoclonal antibody (0.8 mg or 40 mg, respectively), and the flow-through fractions (FT) were collected. The sFlt1 concentrations in the Input and FT fractions were determined using the R&D Flt-1 DuoSet kit (DY321). The % sFlt1 depletion was calculated by the formula, % sFlt1 depletion=[(sFlt1$_{Input}$-sFlt1$_{FT}$)/sFlt1$_{Input}$]. FIG. 10 shows that both 1 mL and 50 mL device columns can deplete nearly all of the sFlt1 protein in serum.

Figure 11:
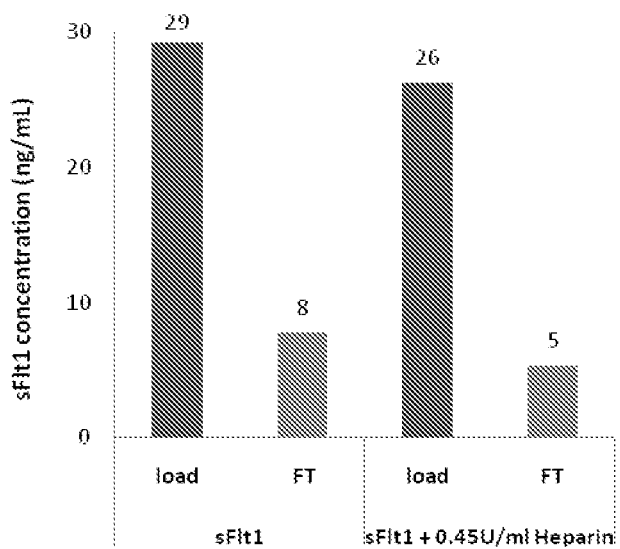
FIG. 11 shows sFlt-1 depletion by antibody AG10B in the presence of heparin.

Heparin does not interfere with sFlt-1 depletion by AG10B. Horse serum containing recombinant sFlt1 with or without 0.45 U of heparin was applied over a 0.1-mL column containing Sepharose beads coupled to AG10B. The samples were assayed for sFlt1 levels before (load) and after (FT) flowing through the AG10B-containing columns. The sFlt1 levels were assayed using the R&D Flt-1 DuoSet kit (DY321). (Table 7, FIG. 11)

TABLE 7

| sFlt-1 levels (ng/ml) | Serum | Serum + Heparin |
|---|---|---|
| Total sFlt-1 | 29.3 | 26.2 |
| sFlt-1 depleted by Ag10B | 21.6 | 20.9 |
| % depletion | 74% | 80% |

Figure 12:
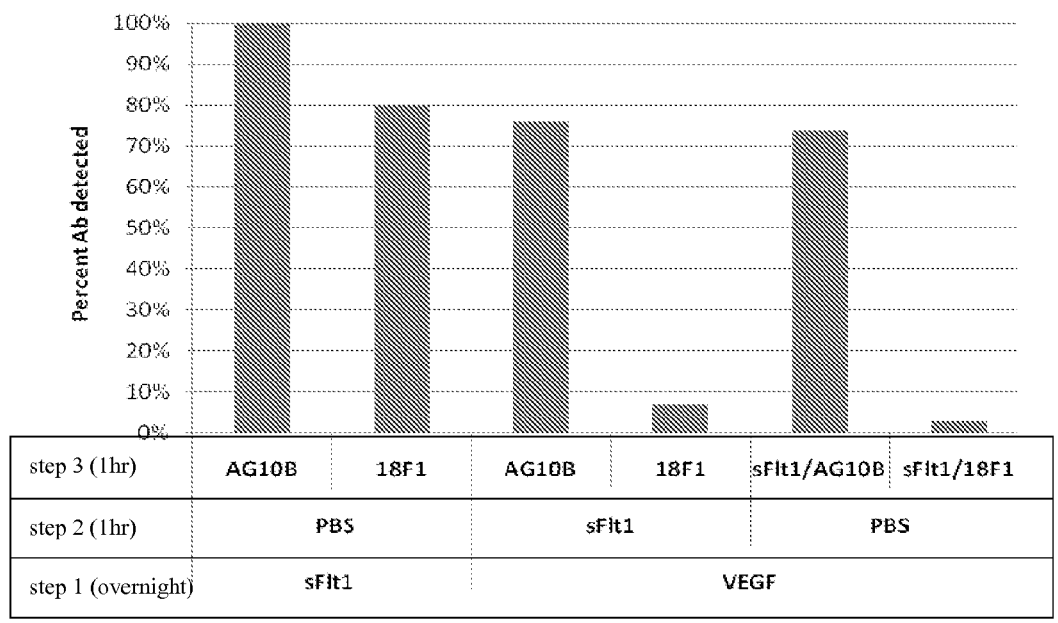
FIG. 12 shows binding of antibody AG10B to sFlt-1 does not block VEGF binding.

AG10B bound to sFlt-1 does not block binding of sFlt-1 to VEGF. As depicted in FIG. 12, ELISA plates were coated with either sFlt1 or VEGF. After washing, PBS was added to well coated with sFlt-1, and either PBS or sFlt1 was added to wells coated with VEGF. After washing, AG10B or 18F1 (an antibody that blocks sFlt1—VEGF interaction) was added to wells containing immobilized VEGF bound to sFlt-1, and sFlt1 pre-complexed with AG10B, or sFlt1 pre-complexed with 18F1 was added to wells coated with PBS. As indicated in FIG. 12, AG10B binds to sFlt1 and sFlt1/VEGF complexes. Pre-complexed sFlt1/AG10B also binds to VEGF. In contrast, 18F1, a blocking antibody, does not bind to sFlt1/VEGF complexes. Similarly, addition of 18F1 to sFlt1 prevents VEGF and sFlt1 interaction.

Figure 13:
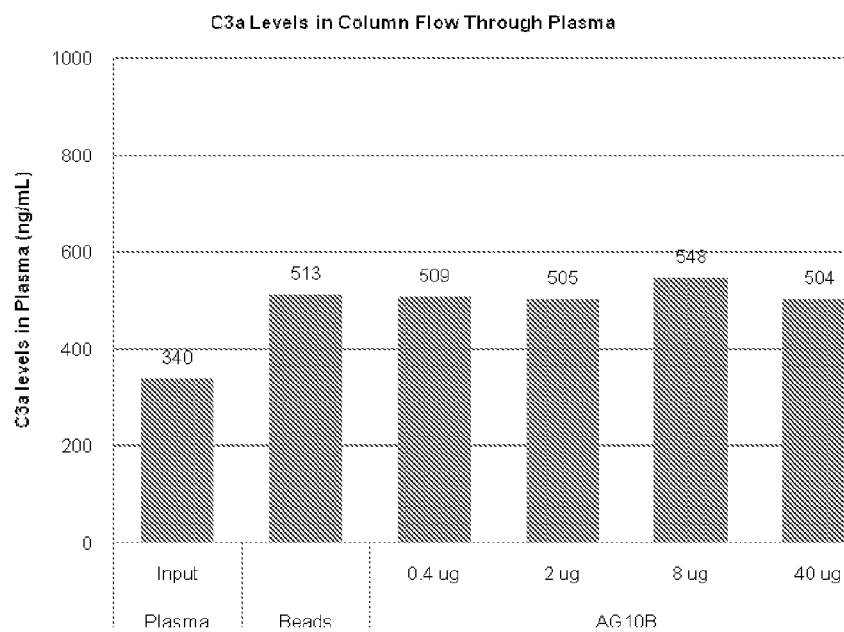
FIG. 13 shows AG10B immobilized on Sepharose beads does not activate the complement system.

Complement Activation—AG10B coupled to beads does not activate the complement system more than beads alone (FIG. 13). Human blood plasma spiked with purified sFlt1 was applied to 0.1-mL columns containing Sepharose beads coupled to purified monoclonal antibody AG10B or a negative control column without antibody (PBS pH 7.4, Beads). Samples were heated to 37° C. and assayed for complement activation product C3a using Quidel MicroVue C3a Plus EIA kit according to the manufacturer's instructions. C3a standards provided in the kit were used to generate a standard curve used to determine the C3a concentrations in the plasma fractions.

AG10B binds to an epitope in the d1-d3 domain of sFlt-1. Table 8 shows that AG10B binds to an epitope on native sFlt1 forms that exist in amniotic fluid (AF) of PE patients as well as two recombinant forms (d1-d3 domain or full-length) of sFlt1. The blocking antibody 18F1 that competes with VEGF for a binding site on sFlt1 is not able to bind as efficiently to sFlt1 (d1-d3) in the presence of VEGF. The 508 antibody cannot bind to sFlt1 (d1-d3) but can bind native sFlt1 isoforms in AF, indicating that its binding epitope on sFlt1 may be located outside of the d1-d3 domain. The negative control antibody Ebx cannot bind to native or recombinant forms of sFlt1.

TABLE 8

| | Native sFlt1 in Amniotic Fluid | Recombinant sFlt1 (d1-d3) | Recombinant sFlt1 (d1-d3) + VEGF | Recombinant sFlt1 full length |
|---|---|---|---|---|
| AG10B | + | + | + | + |
| 18F1 | n.d. | + | +/− | n.d. |
| 508 | + | − | n.d. | − |
| Ebx | − | − | − | − |

What is claimed is:

1. An anti-sFlt-1 antibody which comprises heavy chain CDRs having the amino acid sequence SEQ ID NO:18, SEQ ID NO:20, and SEQ ID NO:22 and light chain CDRs having the amino acid sequence SEQ ID NO:24, SEQ ID NO:26, and SEQ ID NO:28.

2. The anti-sFlt-1 antibody of claim 1, wherein the heavy chain comprises the amino acid sequence SEQ ID NO:30 or a sequence at least 85% identical thereto and the light chain comprises the amino acid sequence SEQ ID NO:32 or a sequence at least 85% identical thereto.

3. The anti-sFlt-1 antibody of claim 1, wherein the anti-sFlt-1 antibody binds to one or more of domains 1-3 of sFlt-1.

4. The anti-sFlt-1 antibody of claim 1, wherein the anti-sFlt-1 antibody does not block ligand binding to sFlt-1.

5. A method of treating eclampsia or pre-eclampsia in a subject comprising providing ex vivo to the subject an anti-sFlt-1 antibody, or sFlt-1 binding fragment thereof, which comprises the anti-sFlt-1 antibody of claim 1.

6. The method of claim 5, wherein the heavy chain comprises the amino acid sequence SEQ ID NO:30 or a sequence at least 85% identical thereto and the light chain comprises the amino acid sequence SEQ ID NO:32 or a sequence at least 85% identical thereto.

7. The method of claim 5, wherein the anti-sFlt-1 antibody binds to one or more of domains 1-3 of sFlt-1.

8. The method of claim 5, wherein the anti-sFlt-1 antibody does not block ligand binding to sFlt-1.

9. The method of claim 5, wherein the pregnancy-related hypertensive disorder is pre-eclampsia.

10. The method of claim 9, wherein the subject is a pregnant human or a post-partum human.

11. The method of claim 10, wherein, the subject is a pregnant human.

12. The method of claim 5, which comprises:
 (a) removing blood from the subject,
 (b) passing the blood or a component thereof over a solid support to which are attached anti-sFlt-1 antibodies, or sFlt-1 binding fragments thereof, to decrease the level of sFlt-1 in the blood or component thereof, and
 (c) returning the blood or component thereof to the subject's body.

13. The method of claim 12, wherein the blood or a component thereof comprises plasma and the method comprises removing a volume of the subject's blood and separating the blood into plasma and cellular components and passing the plasma over the solid support.

14. A system comprising:
 (a) anti-sFlt-1 antibodies, wherein the anti-sFlt-1 antibodies comprise the anti-sFlt-1 antibodies of claim 1, or sFlt-1 binding fragments thereof;
 (b) first means for conveying blood or a component thereof from a subject to the anti-sFlt-1 antibodies, or sFlt-1 binding fragments thereof, bound to the solid support so as to contact the blood or a component thereof with the anti-sFlt-1 antibodies, or sFlt-1 binding fragments thereof, and thereby remove sFlt-1 from the blood or a component thereof; and
 (c) second means for conveying the blood or a component thereof to the subject following contact of the blood or a component thereof with the anti-sFlt-1 antibodies, or sFlt-1 binding fragments thereof.

15. An anti-sFlt-1 antibody or sFlt-1 binding fragment thereof, which competes for binding with an antibody which comprises heavy chain CDRs having the amino acid sequence SEQ ID NO:18, SEQ ID NO:20, and SEQ ID NO:22 and light chain CDRs having the amino acid sequence SEQ ID NO:24, SEQ ID NO:26, and SEQ ID NO:28.

16. The anti-sFlt-1 antibody or sFlt-1 binding fragment of claim 15, wherein the anti-sFlt-1 antibody, or sFlt-1 binding fragment thereof, competes for binding to sFlt-1 with an antibody which comprises a heavy chain.

17. A method of treating eclampsia or pre-eclampsia in a subject comprising providing ex vivo to the subject an anti-sFlt-1 antibody, or sFlt-1 binding fragment thereof which competes for binding with the anti-sFlt-1 antibody or sFlt-1 binding fragment thereof of claim 15.

18. The method of claim 17, wherein the anti-sFlt-1 antibody, or sFlt-1 binding fragment thereof, competes for binding to sFlt-1 with an antibody which comprises the amino acid sequence SEQ ID NO:30.

19. The method of claim 17, wherein the anti-sFlt-1 antibody, or sFlt-1 binding fragment thereof, competes for binding to sFlt-1 with an antibody which comprising a heavy chain having the amino acid sequence SEQ ID NO:30 and a light chain having the amino acid sequence SEQ ID NO:32.

* * * * *

SEQUENCE LISTING

<160> NUMBER OF SEQ ID NOS: 39

<210> SEQ ID NO 1
<211> LENGTH: 15
<212> TYPE: DNA
<213> ORGANISM: Mus musculus
<220> FEATURE:
<221> NAME/KEY: CDS

<222> LOCATION: (1)..(15)

<400> SEQUENCE: 1

```
aat tat ggt gta cat                                              15
Asn Tyr Gly Val His
1               5
```

<210> SEQ ID NO 2
<211> LENGTH: 5
<212> TYPE: PRT
<213> ORGANISM: Mus musculus

<400> SEQUENCE: 2

```
Asn Tyr Gly Val His
1               5
```

<210> SEQ ID NO 3
<211> LENGTH: 48
<212> TYPE: DNA
<213> ORGANISM: Mus musculus
<220> FEATURE:
<221> NAME/KEY: CDS
<222> LOCATION: (1)..(48)

<400> SEQUENCE: 3

```
gtg ata tgg agt ggt gga agc atc gat tat aat gca gtt ttc aca tcc    48
Val Ile Trp Ser Gly Gly Ser Ile Asp Tyr Asn Ala Val Phe Thr Ser
1               5                   10                  15
```

<210> SEQ ID NO 4
<211> LENGTH: 16
<212> TYPE: PRT
<213> ORGANISM: Mus musculus

<400> SEQUENCE: 4

```
Val Ile Trp Ser Gly Gly Ser Ile Asp Tyr Asn Ala Val Phe Thr Ser
1               5                   10                  15
```

<210> SEQ ID NO 5
<211> LENGTH: 42
<212> TYPE: DNA
<213> ORGANISM: Mus musculus
<220> FEATURE:
<221> NAME/KEY: CDS
<222> LOCATION: (1)..(42)

<400> SEQUENCE: 5

```
aat gtg ggc tat agg tac gac gac ggc tat gtt atg gac tac            42
Asn Val Gly Tyr Arg Tyr Asp Asp Gly Tyr Val Met Asp Tyr
1               5                   10
```

<210> SEQ ID NO 6
<211> LENGTH: 14
<212> TYPE: PRT
<213> ORGANISM: Mus musculus

<400> SEQUENCE: 6

```
Asn Val Gly Tyr Arg Tyr Asp Asp Gly Tyr Val Met Asp Tyr
1               5                   10
```

<210> SEQ ID NO 7
<211> LENGTH: 33
<212> TYPE: DNA
<213> ORGANISM: Mus musculus
<220> FEATURE:
<221> NAME/KEY: CDS
<222> LOCATION: (1)..(33)

```
<400> SEQUENCE: 7 aag gcc agt cag agt gtg agt att gat gta gct                          33
Lys Ala Ser Gln Ser Val Ser Ile Asp Val Ala
1               5                   10

<210> SEQ ID NO 8
<211> LENGTH: 11
<212> TYPE: PRT
<213> ORGANISM: Mus musculus

<400> SEQUENCE: 8

Lys Ala Ser Gln Ser Val Ser Ile Asp Val Ala
1               5                   10

<210> SEQ ID NO 9
<211> LENGTH: 21
<212> TYPE: DNA
<213> ORGANISM: Mus musculus
<220> FEATURE:
<221> NAME/KEY: CDS
<222> LOCATION: (1)..(21)

<400> SEQUENCE: 9 cat gca tcc aat cgg tac act                                          21
His Ala Ser Asn Arg Tyr Thr
1               5

<210> SEQ ID NO 10
<211> LENGTH: 7
<212> TYPE: PRT
<213> ORGANISM: Mus musculus

<400> SEQUENCE: 10

His Ala Ser Asn Arg Tyr Thr
1               5

<210> SEQ ID NO 11
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 11 cag cag aat tat gac tct cca ttc acg                                  27
Gln Gln Asn Tyr Asp Ser Pro Phe Thr
1               5

<210> SEQ ID NO 12
<211> LENGTH: 9
<212> TYPE: PRT
<213> ORGANISM: Mus musculus

<400> SEQUENCE: 12

Gln Gln Asn Tyr Asp Ser Pro Phe Thr
1               5

<210> SEQ ID NO 13
<211> LENGTH: 366
<212> TYPE: DNA
<213> ORGANISM: Mus musculus
<220> FEATURE:
<221> NAME/KEY: CDS
<222> LOCATION: (1)..(366)
```

<400> SEQUENCE: 13

```
cag gtg cag ctg aag cag tca gga cct ggc cta gtg cag ccc tca cag      48
Gln Val Gln Leu Lys Gln Ser Gly Pro Gly Leu Val Gln Pro Ser Gln
1               5                   10                  15 agc ctg tcc ctc acc tgc aca gtc tct ggt ttc tca tta act aat tat      96
Ser Leu Ser Leu Thr Cys Thr Val Ser Gly Phe Ser Leu Thr Asn Tyr
            20                  25                  30 ggt gta cat tgg att cgc cag tct cca gga aag ggt ctg gag tgg ctg     144
Gly Val His Trp Ile Arg Gln Ser Pro Gly Lys Gly Leu Glu Trp Leu
        35                  40                  45 gga gtg ata tgg agt ggt gga agc atc gat tat aat gca gtt ttc aca     192
Gly Val Ile Trp Ser Gly Gly Ser Ile Asp Tyr Asn Ala Val Phe Thr
    50                  55                  60 tcc aga ttg acc atc acc aag gac cat tcc aag agc caa gtt ttc ttt     240
Ser Arg Leu Thr Ile Thr Lys Asp His Ser Lys Ser Gln Val Phe Phe
65                  70                  75                  80 aaa gtg aac agt ctg gaa agt aat gac aca gcc ata tat tac tgt gcc     288
Lys Val Asn Ser Leu Glu Ser Asn Asp Thr Ala Ile Tyr Tyr Cys Ala
                85                  90                  95 aga aat gtg ggc tat agg tac gac gac ggc tat gtt atg gac tac tgg     336
Arg Asn Val Gly Tyr Arg Tyr Asp Asp Gly Tyr Val Met Asp Tyr Trp
            100                 105                 110 ggt caa gga acc tca gtc atc gtc tcc tca                             366
Gly Gln Gly Thr Ser Val Ile Val Ser Ser
        115                 120
```

<210> SEQ ID NO 14
<211> LENGTH: 122
<212> TYPE: PRT
<213> ORGANISM: Mus musculus

<400> SEQUENCE: 14

```
Gln Val Gln Leu Lys Gln Ser Gly Pro Gly Leu Val Gln Pro Ser Gln
1               5                   10                  15

Ser Leu Ser Leu Thr Cys Thr Val Ser Gly Phe Ser Leu Thr Asn Tyr
            20                  25                  30

Gly Val His Trp Ile Arg Gln Ser Pro Gly Lys Gly Leu Glu Trp Leu
        35                  40                  45

Gly Val Ile Trp Ser Gly Gly Ser Ile Asp Tyr Asn Ala Val Phe Thr
    50                  55                  60

Ser Arg Leu Thr Ile Thr Lys Asp His Ser Lys Ser Gln Val Phe Phe
65                  70                  75                  80

Lys Val Asn Ser Leu Glu Ser Asn Asp Thr Ala Ile Tyr Tyr Cys Ala
                85                  90                  95

Arg Asn Val Gly Tyr Arg Tyr Asp Asp Gly Tyr Val Met Asp Tyr Trp
            100                 105                 110

Gly Gln Gly Thr Ser Val Ile Val Ser Ser
        115                 120
```

<210> SEQ ID NO 15
<211> LENGTH: 327
<212> TYPE: DNA
<213> ORGANISM: Mus musculus
<220> FEATURE:
<221> NAME/KEY: CDS
<222> LOCATION: (1)..(327)

<400> SEQUENCE: 15

```
agt att gtg atg acc cag act ccc aaa ttc ctg ctt gta tca gca gga      48
Ser Ile Val Met Thr Gln Thr Pro Lys Phe Leu Leu Val Ser Ala Gly
```

```
                1               5                      10                      15
        gac agg gtt acc ata acc tgc aag gcc agt cag agt gtg agt att gat          96
        Asp Arg Val Thr Ile Thr Cys Lys Ala Ser Gln Ser Val Ser Ile Asp
                        20                      25                      30 gta gct tgg tac caa cag aag cca ggg cag tct cct aaa ctt ctg ata         144
        Val Ala Trp Tyr Gln Gln Lys Pro Gly Gln Ser Pro Lys Leu Leu Ile
                    35                      40                      45 tat cat gca tcc aat cgg tac act gga gtc cct gat cgc ttc att gga         192
        Tyr His Ala Ser Asn Arg Tyr Thr Gly Val Pro Asp Arg Phe Ile Gly
                50                      55                      60 agt aga tat ggg acg gat ttc act ttc acc atc agc act gtg cag gct         240
        Ser Arg Tyr Gly Thr Asp Phe Thr Phe Thr Ile Ser Thr Val Gln Ala
        65                      70                      75                      80 gaa gac ctg gca gtt tat ttc tgt cag cag aat tat gac tct cca ttc         288
        Glu Asp Leu Ala Val Tyr Phe Cys Gln Gln Asn Tyr Asp Ser Pro Phe
                        85                      90                      95 acg ttc ggc tcg ggg aca aag ttg gaa tta aaa cgg gct                     327
        Thr Phe Gly Ser Gly Thr Lys Leu Glu Leu Lys Arg Ala
                    100                     105
```

<210> SEQ ID NO 16
<211> LENGTH: 109
<212> TYPE: PRT
<213> ORGANISM: Mus musculus

<400> SEQUENCE: 16

```
Ser Ile Val Met Thr Gln Thr Pro Lys Phe Leu Leu Val Ser Ala Gly
1               5                      10                      15

Asp Arg Val Thr Ile Thr Cys Lys Ala Ser Gln Ser Val Ser Ile Asp
                20                      25                      30

Val Ala Trp Tyr Gln Gln Lys Pro Gly Gln Ser Pro Lys Leu Leu Ile
            35                      40                      45

Tyr His Ala Ser Asn Arg Tyr Thr Gly Val Pro Asp Arg Phe Ile Gly
        50                      55                      60

Ser Arg Tyr Gly Thr Asp Phe Thr Phe Thr Ile Ser Thr Val Gln Ala
65                      70                      75                      80

Glu Asp Leu Ala Val Tyr Phe Cys Gln Gln Asn Tyr Asp Ser Pro Phe
                85                      90                      95

Thr Phe Gly Ser Gly Thr Lys Leu Glu Leu Lys Arg Ala
            100                     105
```

<210> SEQ ID NO 17
<211> LENGTH: 30
<212> TYPE: DNA
<213> ORGANISM: Mus musculus
<220> FEATURE:
<221> NAME/KEY: CDS
<222> LOCATION: (1)..(30)

<400> SEQUENCE: 17

```
gga tac aca ttc act gac tat gtt ata agt                                  30
Gly Tyr Thr Phe Thr Asp Tyr Val Ile Ser
1               5                      10
```

<210> SEQ ID NO 18
<211> LENGTH: 10
<212> TYPE: PRT
<213> ORGANISM: Mus musculus

<400> SEQUENCE: 18

Gly Tyr Thr Phe Thr Asp Tyr Val Ile Ser

<210> SEQ ID NO 19
<211> LENGTH: 60
<212> TYPE: DNA
<213> ORGANISM: Mus musculus
<220> FEATURE:
<221> NAME/KEY: CDS
<222> LOCATION: (1)..(60)

<400> SEQUENCE: 19

```
tgg att gga gag att tat cct gga agt ggt agt att tac tac aat gag      48
Trp Ile Gly Glu Ile Tyr Pro Gly Ser Gly Ser Ile Tyr Tyr Asn Glu
1               5                   10                  15 aag ttc aag ggc                                                       60
Lys Phe Lys Gly
            20
```

<210> SEQ ID NO 20
<211> LENGTH: 20
<212> TYPE: PRT
<213> ORGANISM: Mus musculus

<400> SEQUENCE: 20

```
Trp Ile Gly Glu Ile Tyr Pro Gly Ser Gly Ser Ile Tyr Tyr Asn Glu
1               5                   10                  15

Lys Phe Lys Gly
            20
```

<210> SEQ ID NO 21
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 21

```
ggg cat tat tac ggt tac ttt gac tac                                   27
Gly His Tyr Tyr Gly Tyr Phe Asp Tyr
1               5
```

<210> SEQ ID NO 22
<211> LENGTH: 9
<212> TYPE: PRT
<213> ORGANISM: Mus musculus

<400> SEQUENCE: 22

```
Gly His Tyr Tyr Gly Tyr Phe Asp Tyr
1               5
```

<210> SEQ ID NO 23
<211> LENGTH: 39
<212> TYPE: DNA
<213> ORGANISM: Mus musculus
<220> FEATURE:
<221> NAME/KEY: CDS
<222> LOCATION: (1)..(39)

<400> SEQUENCE: 23

```
aag gcc agt cag gat gtg act att act gta gcc tgg tat                   39
Lys Ala Ser Gln Asp Val Thr Ile Thr Val Ala Trp Tyr
1               5                   10
```

<210> SEQ ID NO 24
<211> LENGTH: 13

```
<212> TYPE: PRT
<213> ORGANISM: Mus musculus

<400> SEQUENCE: 24

Lys Ala Ser Gln Asp Val Thr Ile Thr Val Ala Trp Tyr
1               5                   10

<210> SEQ ID NO 25
<211> LENGTH: 33
<212> TYPE: DNA
<213> ORGANISM: Mus musculus
<220> FEATURE:
<221> NAME/KEY: CDS
<222> LOCATION: (1)..(33)

<400> SEQUENCE: 25 ctt ctg att tac tcg gca tcc tac cgg tac act                          33
Leu Leu Ile Tyr Ser Ala Ser Tyr Arg Tyr Thr
1               5                   10

<210> SEQ ID NO 26
<211> LENGTH: 11
<212> TYPE: PRT
<213> ORGANISM: Mus musculus

<400> SEQUENCE: 26

Leu Leu Ile Tyr Ser Ala Ser Tyr Arg Tyr Thr
1               5                   10

<210> SEQ ID NO 27
<211> LENGTH: 27
<212> TYPE: DNA
<213> ORGANISM: Mus musculus
<220> FEATURE:
<221> NAME/KEY: CDS
<222> LOCATION: (1)..(27)

<400> SEQUENCE: 27 cag caa cat tat act act ccg tgg acg                                  27
Gln Gln His Tyr Thr Thr Pro Trp Thr
1               5

<210> SEQ ID NO 28
<211> LENGTH: 9
<212> TYPE: PRT
<213> ORGANISM: Mus musculus

<400> SEQUENCE: 28

Gln Gln His Tyr Thr Thr Pro Trp Thr
1               5

<210> SEQ ID NO 29
<211> LENGTH: 354
<212> TYPE: DNA
<213> ORGANISM: Mus musculus
<220> FEATURE:
<221> NAME/KEY: CDS
<222> LOCATION: (1)..(354)

<400> SEQUENCE: 29 cag gtt cag ctg cag cag tct gga cct gag ctg gtg aag cct ggg gct     48
Gln Val Gln Leu Gln Gln Ser Gly Pro Glu Leu Val Lys Pro Gly Ala
1               5                   10                  15 tca gtg aag atg tcc tgc aag gct tct gga tac aca ttc act gac tat     96
Ser Val Lys Met Ser Cys Lys Ala Ser Gly Tyr Thr Phe Thr Asp Tyr
            20                  25                  30
```

```
gtt ata agt tgg gtg aaa cag aga act gga cag ggc ctt gag tgg att    144
Val Ile Ser Trp Val Lys Gln Arg Thr Gly Gln Gly Leu Glu Trp Ile
         35                  40                  45 gga gag att tat cct gga agt ggt agt att tac tac aat gag aag ttc    192
Gly Glu Ile Tyr Pro Gly Ser Gly Ser Ile Tyr Tyr Asn Glu Lys Phe
     50                  55                  60 aag ggc aag gcc aca ctg act gca gac aca tcc tcc aac aca gcc tac    240
Lys Gly Lys Ala Thr Leu Thr Ala Asp Thr Ser Ser Asn Thr Ala Tyr
 65                  70                  75                  80 atg cag ctc agc agc ctg aca ttt gag gac tct gcg gtc att ttc tgt    288
Met Gln Leu Ser Ser Leu Thr Phe Glu Asp Ser Ala Val Ile Phe Cys
                 85                  90                  95 gca aga ggg cat tat tac ggt tac ttt gac tac tgg ggc caa ggc acc    336
Ala Arg Gly His Tyr Tyr Gly Tyr Phe Asp Tyr Trp Gly Gln Gly Thr
                100                 105                 110 act ctc aca gtc tcc tca                                            354
Thr Leu Thr Val Ser Ser
        115

<210> SEQ ID NO 30
<211> LENGTH: 118
<212> TYPE: PRT
<213> ORGANISM: Mus musculus

<400> SEQUENCE: 30

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Ile Tyr Tyr Asn Glu Lys Phe
    50                  55                  60

Lys Gly Lys Ala Thr Leu Thr Ala Asp Thr Ser Ser Asn Thr Ala Tyr
65                  70                  75                  80

Met Gln Leu Ser Ser Leu Thr Phe Glu Asp Ser Ala Val Ile Phe Cys
                85                  90                  95

Ala Arg Gly His Tyr Tyr Gly Tyr Phe Asp Tyr Trp Gly Gln Gly Thr
                100                 105                 110

Thr Leu Thr Val Ser Ser
        115

<210> SEQ ID NO 31
<211> LENGTH: 327
<212> TYPE: DNA
<213> ORGANISM: Mus musculus
<220> FEATURE:
<221> NAME/KEY: CDS
<222> LOCATION: (1)..(327)

<400> SEQUENCE: 31 gac att gtg atg acc cag tct cac aaa ttc atg tcc aca tca gta gga     48
Asp Ile Val Met Thr Gln Ser His Lys Phe Met Ser Thr Ser Val Gly
1               5                   10                  15 gac agg gtc agc atc acc tgc aag gcc agt cag gat gtg act att act     96
Asp Arg Val Ser Ile Thr Cys Lys Ala Ser Gln Asp Val Thr Ile Thr
            20                  25                  30 gta gcc tgg tat caa cag aaa cca gga caa tct cct aaa ctt ctg att    144
Val Ala Trp Tyr Gln Gln Lys Pro Gly Gln Ser Pro Lys Leu Leu Ile
        35                  40                  45
```

| | | | | | | | | | | | | | | | | |
|---|---|---|---|---|---|---|---|---|---|---|---|---|---|---|---|---|
| tac | tcg | gca | tcc | tac | cgg | tac | act | gga | gtc | cct | gat | cgc | ttc | act | ggc | 192 |
| Tyr | Ser | Ala | Ser | Tyr | Arg | Tyr | Thr | Gly | Val | Pro | Asp | Arg | Phe | Thr | Gly | |
| | | | 50 | | | | 55 | | | | 60 | | | | | |
| agt | gga | tct | ggg | acg | gat | ttc | act | ttc | acc | atc | agc | agt | gtg | cag | gct | 240 |
| Ser | Gly | Ser | Gly | Thr | Asp | Phe | Thr | Phe | Thr | Ile | Ser | Ser | Val | Gln | Ala | |
| 65 | | | | | 70 | | | | 75 | | | | | 80 | | |
| gaa | gac | ctg | gca | gtt | tat | tac | tgt | cag | caa | cat | tat | act | act | ccg | tgg | 288 |
| Glu | Asp | Leu | Ala | Val | Tyr | Tyr | Cys | Gln | Gln | His | Tyr | Thr | Thr | Pro | Trp | |
| | | | | 85 | | | | | 90 | | | | 95 | | | |
| acg | ttc | ggt | gga | ggc | acc | aag | ctg | gaa | atc | aaa | cgg | gct | | | | 327 |
| Thr | Phe | Gly | Gly | Gly | Thr | Lys | Leu | Glu | Ile | Lys | Arg | Ala | | | | |
| | | 100 | | | | | 105 | | | | | | | | | |

<210> SEQ ID NO 32
<211> LENGTH: 109
<212> TYPE: PRT
<213> ORGANISM: Mus musculus

<400> SEQUENCE: 32

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Thr Ile Thr
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Trp
                85                  90                  95

Thr Phe Gly Gly Gly Thr Lys Leu Glu Ile Lys Arg Ala
            100                 105

<210> SEQ ID NO 33
<211> LENGTH: 4017
<212> TYPE: DNA
<213> ORGANISM: Homo sapiens
<220> FEATURE:
<221> NAME/KEY: CDS
<222> LOCATION: (1)..(4017)

<400> SEQUENCE: 33

| | | | | | | | | | | | | | | | | |
|---|---|---|---|---|---|---|---|---|---|---|---|---|---|---|---|---|
| atg | gtc | agc | tac | tgg | gac | acc | ggg | gtc | ctg | ctg | tgc | gcg | ctg | ctc | agc | 48 |
| Met | Val | Ser | Tyr | Trp | Asp | Thr | Gly | Val | Leu | Leu | Cys | Ala | Leu | Leu | Ser | |
| 1 | | | | 5 | | | | | 10 | | | | | 15 | | |
| tgt | ctg | ctt | ctc | aca | gga | tct | agt | tca | ggt | tca | aaa | tta | aaa | gat | cct | 96 |
| Cys | Leu | Leu | Leu | Thr | Gly | Ser | Ser | Ser | Gly | Ser | Lys | Leu | Lys | Asp | Pro | |
| | | | 20 | | | | | 25 | | | | | 30 | | | |
| gaa | ctg | agt | tta | aaa | ggc | acc | cag | cac | atc | atg | caa | gca | ggc | cag | aca | 144 |
| Glu | Leu | Ser | Leu | Lys | Gly | Thr | Gln | His | Ile | Met | Gln | Ala | Gly | Gln | Thr | |
| | | | | 35 | | | | | 40 | | | | | 45 | | |
| ctg | cat | ctc | caa | tgc | agg | ggg | gaa | gca | gcc | cat | aaa | tgg | tct | ttg | cct | 192 |
| Leu | His | Leu | Gln | Cys | Arg | Gly | Glu | Ala | Ala | His | Lys | Trp | Ser | Leu | Pro | |
| | | 50 | | | | | 55 | | | | | 60 | | | | |
| gaa | atg | gtg | agt | aag | gaa | agc | gaa | agg | ctg | agc | ata | act | aaa | tct | gcc | 240 |
| Glu | Met | Val | Ser | Lys | Glu | Ser | Glu | Arg | Leu | Ser | Ile | Thr | Lys | Ser | Ala | |
| 65 | | | | | 70 | | | | | 75 | | | | | 80 | |
| tgt | gga | aga | aat | ggc | aaa | caa | ttc | tgc | agt | act | tta | acc | ttg | aac | aca | 288 |
| Cys | Gly | Arg | Asn | Gly | Lys | Gln | Phe | Cys | Ser | Thr | Leu | Thr | Leu | Asn | Thr | |
| | | | | 85 | | | | | 90 | | | | | 95 | | |

```
gct caa gca aac cac act ggc ttc tac agc tgc aaa tat cta gct gta    336
Ala Gln Ala Asn His Thr Gly Phe Tyr Ser Cys Lys Tyr Leu Ala Val
            100                 105                 110 cct act tca aag aag aag gaa aca gaa tct gca atc tat ata ttt att    384
Pro Thr Ser Lys Lys Lys Glu Thr Glu Ser Ala Ile Tyr Ile Phe Ile
        115                 120                 125 agt gat aca ggt aga cct ttc gta gag atg tac agt gaa atc ccc gaa    432
Ser Asp Thr Gly Arg Pro Phe Val Glu Met Tyr Ser Glu Ile Pro Glu
130                 135                 140 att ata cac atg act gaa gga agg gag ctc gtc att ccc tgc cgg gtt    480
Ile Ile His Met Thr Glu Gly Arg Glu Leu Val Ile Pro Cys Arg Val
145                 150                 155                 160 acg tca cct aac atc act gtt act tta aaa aag ttt cca ctt gac act    528
Thr Ser Pro Asn Ile Thr Val Thr Leu Lys Lys Phe Pro Leu Asp Thr
                165                 170                 175 ttg atc cct gat gga aaa cgc ata atc tgg gac agt aga aag ggc ttc    576
Leu Ile Pro Asp Gly Lys Arg Ile Ile Trp Asp Ser Arg Lys Gly Phe
            180                 185                 190 atc ata tca aat gca acg tac aaa gaa ata ggg ctt ctg acc tgt gaa    624
Ile Ile Ser Asn Ala Thr Tyr Lys Glu Ile Gly Leu Leu Thr Cys Glu
        195                 200                 205 gca aca gtc aat ggg cat ttg tat aag aca aac tat ctc aca cat cga    672
Ala Thr Val Asn Gly His Leu Tyr Lys Thr Asn Tyr Leu Thr His Arg
    210                 215                 220 caa acc aat aca atc ata gat gtc caa ata agc aca cca cgc cca gtc    720
Gln Thr Asn Thr Ile Ile Asp Val Gln Ile Ser Thr Pro Arg Pro Val
225                 230                 235                 240 aaa tta ctt aga ggc cat act ctt gtc ctc aat tgt act gct acc act    768
Lys Leu Leu Arg Gly His Thr Leu Val Leu Asn Cys Thr Ala Thr Thr
                245                 250                 255 ccc ttg aac acg aga gtt caa atg acc tgg agt tac cct gat gaa aaa    816
Pro Leu Asn Thr Arg Val Gln Met Thr Trp Ser Tyr Pro Asp Glu Lys
            260                 265                 270 aat aag aga gct tcc gta agg cga cga att gac caa agc aat tcc cat    864
Asn Lys Arg Ala Ser Val Arg Arg Arg Ile Asp Gln Ser Asn Ser His
        275                 280                 285 gcc aac ata ttc tac agt gtt ctt act att gac aaa atg cag aac aaa    912
Ala Asn Ile Phe Tyr Ser Val Leu Thr Ile Asp Lys Met Gln Asn Lys
    290                 295                 300 gac aaa gga ctt tat act tgt cgt gta agg agt gga cca tca ttc aaa    960
Asp Lys Gly Leu Tyr Thr Cys Arg Val Arg Ser Gly Pro Ser Phe Lys
305                 310                 315                 320 tct gtt aac acc tca gtg cat ata tat gat aaa gca ttc atc act gtg    1008
Ser Val Asn Thr Ser Val His Ile Tyr Asp Lys Ala Phe Ile Thr Val
                325                 330                 335 aaa cat cga aaa cag cag gtg ctt gaa acc gta gct ggc aag cgg tct    1056
Lys His Arg Lys Gln Gln Val Leu Glu Thr Val Ala Gly Lys Arg Ser
            340                 345                 350 tac cgg ctc tct atg aaa gtg aag gca ttt ccc tcg ccg gaa gtt gta    1104
Tyr Arg Leu Ser Met Lys Val Lys Ala Phe Pro Ser Pro Glu Val Val
        355                 360                 365 tgg tta aaa gat ggg tta cct gcg act gag aaa tct gct cgc tat ttg    1152
Trp Leu Lys Asp Gly Leu Pro Ala Thr Glu Lys Ser Ala Arg Tyr Leu
    370                 375                 380 act cgt ggc tac tcg tta att atc aag gac gta act gaa gag gat gca    1200
Thr Arg Gly Tyr Ser Leu Ile Ile Lys Asp Val Thr Glu Glu Asp Ala
385                 390                 395                 400 ggg aat tat aca atc ttg ctg agc ata aaa cag tca aat gtg ttt aaa    1248
Gly Asn Tyr Thr Ile Leu Leu Ser Ile Lys Gln Ser Asn Val Phe Lys
```

-continued

```
                     405                 410                 415
aac ctc act gcc act cta att gtc aat gtg aaa ccc cag att tac gaa         1296
Asn Leu Thr Ala Thr Leu Ile Val Asn Val Lys Pro Gln Ile Tyr Glu
            420                 425                 430 aag gcc gtg tca tcg ttt cca gac ccg gct ctc tac cca ctg ggc agc         1344
Lys Ala Val Ser Ser Phe Pro Asp Pro Ala Leu Tyr Pro Leu Gly Ser
                435                 440                 445 aga caa atc ctg act tgt acc gca tat ggt atc cct caa cct aca atc         1392
Arg Gln Ile Leu Thr Cys Thr Ala Tyr Gly Ile Pro Gln Pro Thr Ile
    450                 455                 460 aag tgg ttc tgg cac ccc tgt aac cat aat cat tcc gaa gca agg tgt         1440
Lys Trp Phe Trp His Pro Cys Asn His Asn His Ser Glu Ala Arg Cys
465                 470                 475                 480 gac ttt tgt tcc aat aat gaa gag tcc tct atc ctg gat gct gac agc         1488
Asp Phe Cys Ser Asn Asn Glu Glu Ser Ser Ile Leu Asp Ala Asp Ser
                485                 490                 495 aac atg gga aac aga att gag agc atc act cag cgc atg gca ata ata         1536
Asn Met Gly Asn Arg Ile Glu Ser Ile Thr Gln Arg Met Ala Ile Ile
            500                 505                 510 gaa gga aag aat aag atg gct agc acc ttg gtt gtg gct gac tct aga         1584
Glu Gly Lys Asn Lys Met Ala Ser Thr Leu Val Val Ala Asp Ser Arg
        515                 520                 525 att tct gga atc tac att tgc ata gct tcc aat aaa gtt ggg act gtg         1632
Ile Ser Gly Ile Tyr Ile Cys Ile Ala Ser Asn Lys Val Gly Thr Val
530                 535                 540 gga aga aac ata agc ttt tat atc aca gat gtg cca aat ggg ttt cat         1680
Gly Arg Asn Ile Ser Phe Tyr Ile Thr Asp Val Pro Asn Gly Phe His
545                 550                 555                 560 gtt aac ttg gaa aaa atg ccg acg gaa gga gag gac ctg aaa ctg tct         1728
Val Asn Leu Glu Lys Met Pro Thr Glu Gly Glu Asp Leu Lys Leu Ser
                565                 570                 575 tgc aca gtt aac aag ttc tta tac aga gac gtt act tgg att tta ctg         1776
Cys Thr Val Asn Lys Phe Leu Tyr Arg Asp Val Thr Trp Ile Leu Leu
            580                 585                 590 cgg aca gtt aat aac aga aca atg cac tac agt att agc aag caa aaa         1824
Arg Thr Val Asn Asn Arg Thr Met His Tyr Ser Ile Ser Lys Gln Lys
        595                 600                 605 atg gcc atc act aag gag cac tcc atc act ctt aat ctt acc atc atg         1872
Met Ala Ile Thr Lys Glu His Ser Ile Thr Leu Asn Leu Thr Ile Met
    610                 615                 620 aat gtt tcc ctg caa gat tca ggc acc tat gcc tgc aga gcc agg aat         1920
Asn Val Ser Leu Gln Asp Ser Gly Thr Tyr Ala Cys Arg Ala Arg Asn
625                 630                 635                 640 gta tac aca ggg gaa gaa atc ctc cag aag aaa gaa att aca atc aga         1968
Val Tyr Thr Gly Glu Glu Ile Leu Gln Lys Lys Glu Ile Thr Ile Arg
                645                 650                 655 gat cag gaa gca cca tac ctc ctg cga aac ctc agt gat cac aca gtg         2016
Asp Gln Glu Ala Pro Tyr Leu Leu Arg Asn Leu Ser Asp His Thr Val
            660                 665                 670 gcc atc agc agt tcc acc act tta gac tgt cat gct aat ggt gtc ccc         2064
Ala Ile Ser Ser Ser Thr Thr Leu Asp Cys His Ala Asn Gly Val Pro
        675                 680                 685 gag cct cag atc act tgg ttt aaa aac aac cac aaa ata caa caa gag         2112
Glu Pro Gln Ile Thr Trp Phe Lys Asn Asn His Lys Ile Gln Gln Glu
    690                 695                 700 cct gga att att tta gga cca gga agc agc acg ctg ttt att gaa aga         2160
Pro Gly Ile Ile Leu Gly Pro Gly Ser Ser Thr Leu Phe Ile Glu Arg
705                 710                 715                 720 gtc aca gaa gag gat gaa ggt gtc tat cac tgc aaa gcc acc aac cag         2208
```

```
                                               -continued

Val Thr Glu Glu Asp Glu Gly Val Tyr His Cys Lys Ala Thr Asn Gln
                    725                 730                 735 aag ggc tct gtg gaa agt tca gca tac ctc act gtt caa gga acc tcg      2256
Lys Gly Ser Val Glu Ser Ser Ala Tyr Leu Thr Val Gln Gly Thr Ser
            740                 745                 750 gac aag tct aat ctg gag ctg atc act cta aca tgc acc tgt gtg gct      2304
Asp Lys Ser Asn Leu Glu Leu Ile Thr Leu Thr Cys Thr Cys Val Ala
            755                 760                 765 gcg act ctc ttc tgg ctc cta tta acc ctc ttt atc cga aaa atg aaa      2352
Ala Thr Leu Phe Trp Leu Leu Leu Thr Leu Phe Ile Arg Lys Met Lys
        770                 775                 780 agg tct tct tct gaa ata aag act gac tac cta tca att ata atg gac      2400
Arg Ser Ser Ser Glu Ile Lys Thr Asp Tyr Leu Ser Ile Ile Met Asp
785                 790                 795                 800 cca gat gaa gtt cct ttg gat gag cag tgt gag cgg ctc cct tat gat      2448
Pro Asp Glu Val Pro Leu Asp Glu Gln Cys Glu Arg Leu Pro Tyr Asp
                805                 810                 815 gcc agc aag tgg gag ttt gcc cgg gag aga ctt aaa ctg ggc aaa tca      2496
Ala Ser Lys Trp Glu Phe Ala Arg Glu Arg Leu Lys Leu Gly Lys Ser
            820                 825                 830 ctt gga aga ggg gct ttt gga aaa gtg gtt caa gca tca gca ttt ggc      2544
Leu Gly Arg Gly Ala Phe Gly Lys Val Val Gln Ala Ser Ala Phe Gly
            835                 840                 845 att aag aaa tca cct acg tgc cgg act gtg gct gtg aaa atg ctg aaa      2592
Ile Lys Lys Ser Pro Thr Cys Arg Thr Val Ala Val Lys Met Leu Lys
850                 855                 860 gag ggg gcc acg gcc agc gag tac aaa gct ctg atg act gag cta aaa      2640
Glu Gly Ala Thr Ala Ser Glu Tyr Lys Ala Leu Met Thr Glu Leu Lys
865                 870                 875                 880 atc ttg acc cac att ggc cac cat ctg aac gtg gtt aac ctg cta gga      2688
Ile Leu Thr His Ile Gly His His Leu Asn Val Val Asn Leu Leu Gly
                885                 890                 895 gcc tgc acc aag caa gga ggg cct ctg atg gtg att gtt gaa tac tgc      2736
Ala Cys Thr Lys Gln Gly Gly Pro Leu Met Val Ile Val Glu Tyr Cys
            900                 905                 910 aaa tat gga aat ctc tcc aac tac ctc aag agc aaa cgt gac tta ttt      2784
Lys Tyr Gly Asn Leu Ser Asn Tyr Leu Lys Ser Lys Arg Asp Leu Phe
            915                 920                 925 ttt ctc aac aag gat gca gca cta cac atg gag cct aag aaa gaa aaa      2832
Phe Leu Asn Lys Asp Ala Ala Leu His Met Glu Pro Lys Lys Glu Lys
        930                 935                 940 atg gag cca ggc ctg gaa caa ggc aag aaa cca aga cta gat agc gtc      2880
Met Glu Pro Gly Leu Glu Gln Gly Lys Lys Pro Arg Leu Asp Ser Val
945                 950                 955                 960 acc agc agc gaa agc ttt gcg agc tcc ggc ttt cag gaa gat aaa agt      2928
Thr Ser Ser Glu Ser Phe Ala Ser Ser Gly Phe Gln Glu Asp Lys Ser
                965                 970                 975 ctg agt gat gtt gag gaa gag gag gat tct gac ggt ttc tac aag gag      2976
Leu Ser Asp Val Glu Glu Glu Glu Asp Ser Asp Gly Phe Tyr Lys Glu
            980                 985                 990 ccc atc act atg gaa gat ctg att  tct tac agt ttt caa  gtg gcc aga    3024
Pro Ile Thr Met Glu Asp Leu Ile  Ser Tyr Ser Phe Gln  Val Ala Arg
            995                 1000                 1005 ggc atg gag ttc ctg tct tcc aga aag tgc att cat  cgg gac ctg         3069
Gly Met Glu Phe Leu Ser Ser Arg Lys Cys Ile His  Arg Asp Leu
        1010                1015                 1020 gca gcg aga aac att ctt tta tct gag aac aac gtg gtg aag att          3114
Ala Ala Arg Asn Ile Leu Leu Ser Glu Asn Asn Val Val Lys Ile
        1025                 1030                 1035
```

```
                                      -continued tgt gat ttt ggc ctt gcc cgg gat att tat aag aac ccc gat tat      3159
Cys Asp Phe Gly Leu Ala Arg Asp Ile Tyr Lys Asn Pro Asp Tyr
1040                1045                1050 gtg aga aaa gga gat act cga ctt cct ctg aaa tgg atg gct cct      3204
Val Arg Lys Gly Asp Thr Arg Leu Pro Leu Lys Trp Met Ala Pro
1055                1060                1065 gaa tct atc ttt gac aaa atc tac agc acc aag agc gac gtg tgg      3249
Glu Ser Ile Phe Asp Lys Ile Tyr Ser Thr Lys Ser Asp Val Trp
1070                1075                1080 tct tac gga gta ttg ctg tgg gaa atc ttc tcc tta ggt ggg tct      3294
Ser Tyr Gly Val Leu Leu Trp Glu Ile Phe Ser Leu Gly Gly Ser
1085                1090                1095 cca tac cca gga gta caa atg gat gag gac ttt tgc agt cgc ctg      3339
Pro Tyr Pro Gly Val Gln Met Asp Glu Asp Phe Cys Ser Arg Leu
1100                1105                1110 agg gaa ggc atg agg atg aga gct cct gag tac tct act cct gaa      3384
Arg Glu Gly Met Arg Met Arg Ala Pro Glu Tyr Ser Thr Pro Glu
1115                1120                1125 atc tat cag atc atg ctg gac tgc tgg cac aga gac cca aaa gaa      3429
Ile Tyr Gln Ile Met Leu Asp Cys Trp His Arg Asp Pro Lys Glu
1130                1135                1140 agg cca aga ttt gca gaa ctt gtg gaa aaa cta ggt gat ttg ctt      3474
Arg Pro Arg Phe Ala Glu Leu Val Glu Lys Leu Gly Asp Leu Leu
1145                1150                1155 caa gca aat gta caa cag gat ggt aaa gac tac atc cca atc aat      3519
Gln Ala Asn Val Gln Gln Asp Gly Lys Asp Tyr Ile Pro Ile Asn
1160                1165                1170 gcc ata ctg aca gga aat agt ggg ttt aca tac tca act cct gcc      3564
Ala Ile Leu Thr Gly Asn Ser Gly Phe Thr Tyr Ser Thr Pro Ala
1175                1180                1185 ttc tct gag gac ttc ttc aag gaa agt att tca gct ccg aag ttt      3609
Phe Ser Glu Asp Phe Phe Lys Glu Ser Ile Ser Ala Pro Lys Phe
1190                1195                1200 aat tca gga agc tct gat gat gtc aga tat gta aat gct ttc aag      3654
Asn Ser Gly Ser Ser Asp Asp Val Arg Tyr Val Asn Ala Phe Lys
1205                1210                1215 ttc atg agc ctg gaa aga atc aaa acc ttt gaa gaa ctt tta ccg      3699
Phe Met Ser Leu Glu Arg Ile Lys Thr Phe Glu Glu Leu Leu Pro
1220                1225                1230 aat gcc acc tcc atg ttt gat gac tac cag ggc gac agc agc act      3744
Asn Ala Thr Ser Met Phe Asp Asp Tyr Gln Gly Asp Ser Ser Thr
1235                1240                1245 ctg ttg gcc tct ccc atg ctg aag cgc ttc acc tgg act gac agc      3789
Leu Leu Ala Ser Pro Met Leu Lys Arg Phe Thr Trp Thr Asp Ser
1250                1255                1260 aaa ccc aag gcc tcg ctc aag att gac ttg aga gta acc agt aaa      3834
Lys Pro Lys Ala Ser Leu Lys Ile Asp Leu Arg Val Thr Ser Lys
1265                1270                1275 agt aag gag tcg ggg ctg tct gat gtc agc agg ccc agt ttc tgc      3879
Ser Lys Glu Ser Gly Leu Ser Asp Val Ser Arg Pro Ser Phe Cys
1280                1285                1290 cat tcc agc tgt ggg cac gtc agc gaa ggc aag cgc agg ttc acc      3924
His Ser Ser Cys Gly His Val Ser Glu Gly Lys Arg Arg Phe Thr
1295                1300                1305 tac gac cac gct gag ctg gaa agg aaa atc gcg tgc tgc tcc ccg      3969
Tyr Asp His Ala Glu Leu Glu Arg Lys Ile Ala Cys Cys Ser Pro
1310                1315                1320 ccc cca gac tac aac tcg gtg gtc ctg tac tcc acc cca ccc atc      4014
Pro Pro Asp Tyr Asn Ser Val Val Leu Tyr Ser Thr Pro Pro Ile
1325                1330                1335
```

| tag | 4017 |

<210> SEQ ID NO 34
<211> LENGTH: 1338
<212> TYPE: PRT
<213> ORGANISM: Homo sapiens

<400> SEQUENCE: 34

```
Met Val Ser Tyr Trp Asp Thr Gly Val Leu Leu Cys Ala Leu Leu Ser
  1               5                  10                  15

Cys Leu Leu Leu Thr Gly Ser Ser Ser Gly Ser Lys Leu Lys Asp Pro
             20                  25                  30

Glu Leu Ser Leu Lys Gly Thr Gln His Ile Met Gln Ala Gly Gln Thr
         35                  40                  45

Leu His Leu Gln Cys Arg Gly Glu Ala Ala His Lys Trp Ser Leu Pro
     50                  55                  60

Glu Met Val Ser Lys Glu Ser Glu Arg Leu Ser Ile Thr Lys Ser Ala
 65                  70                  75                  80

Cys Gly Arg Asn Gly Lys Gln Phe Cys Ser Thr Leu Thr Leu Asn Thr
                 85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365
```

```
Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Ser Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
        755                 760                 765

Ala Thr Leu Phe Trp Leu Leu Leu Thr Leu Phe Ile Arg Lys Met Lys
    770                 775                 780
```

-continued

Arg Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
            805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
            835                 840                 845

Ile Lys Lys Ser Pro Thr Cys Arg Thr Val Ala Val Lys Met Leu Lys
            850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
            885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
            915                 920                 925

Phe Leu Asn Lys Asp Ala Ala Leu His Met Glu Pro Lys Lys Glu Lys
            930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
            995                 1000                1005

Gly Met Glu Phe Leu Ser Ser Arg Lys Cys Ile His Arg Asp Leu
    1010                1015                1020

Ala Ala Arg Asn Ile Leu Leu Ser Glu Asn Asn Val Val Lys Ile
    1025                1030                1035

Cys Asp Phe Gly Leu Ala Arg Asp Ile Tyr Lys Asn Pro Asp Tyr
    1040                1045                1050

Val Arg Lys Gly Asp Thr Arg Leu Pro Leu Lys Trp Met Ala Pro
    1055                1060                1065

Glu Ser Ile Phe Asp Lys Ile Tyr Ser Thr Lys Ser Asp Val Trp
    1070                1075                1080

Ser Tyr Gly Val Leu Leu Trp Glu Ile Phe Ser Leu Gly Gly Ser
    1085                1090                1095

Pro Tyr Pro Gly Val Gln Met Asp Glu Asp Phe Cys Ser Arg Leu
    1100                1105                1110

Arg Glu Gly Met Arg Met Arg Ala Pro Glu Tyr Ser Thr Pro Glu
    1115                1120                1125

Ile Tyr Gln Ile Met Leu Asp Cys Trp His Arg Asp Pro Lys Glu
    1130                1135                1140

Arg Pro Arg Phe Ala Glu Leu Val Glu Lys Leu Gly Asp Leu Leu
    1145                1150                1155

Gln Ala Asn Val Gln Gln Asp Gly Lys Asp Tyr Ile Pro Ile Asn
    1160                1165                1170

Ala Ile Leu Thr Gly Asn Ser Gly Phe Thr Tyr Ser Thr Pro Ala
    1175                1180                1185

Phe Ser Glu Asp Phe Phe Lys Glu Ser Ile Ser Ala Pro Lys Phe

```
                    1190                1195                1200
Asn  Ser  Gly  Ser  Ser  Asp  Asp  Val  Arg  Tyr  Val  Asn  Ala  Phe  Lys
          1205                1210                1215

Phe  Met  Ser  Leu  Glu  Arg  Ile  Lys  Thr  Phe  Glu  Glu  Leu  Leu  Pro
     1220                1225                1230

Asn  Ala  Thr  Ser  Met  Phe  Asp  Asp  Tyr  Gln  Gly  Asp  Ser  Ser  Thr
1235                1240                1245

Leu  Leu  Ala  Ser  Pro  Met  Leu  Lys  Arg  Phe  Thr  Trp  Thr  Asp  Ser
     1250                1255                1260

Lys  Pro  Lys  Ala  Ser  Leu  Lys  Ile  Asp  Leu  Arg  Val  Thr  Ser  Lys
1265                1270                1275

Ser  Lys  Glu  Ser  Gly  Leu  Ser  Asp  Val  Ser  Arg  Pro  Ser  Phe  Cys
     1280                1285                1290

His  Ser  Ser  Cys  Gly  His  Val  Ser  Glu  Gly  Lys  Arg  Arg  Phe  Thr
1295                1300                1305

Tyr  Asp  His  Ala  Glu  Leu  Glu  Arg  Lys  Ile  Ala  Cys  Cys  Ser  Pro
     1310                1315                1320

Pro  Pro  Asp  Tyr  Asn  Ser  Val  Val  Leu  Tyr  Ser  Thr  Pro  Pro  Ile
1325                1330                1335

<210> SEQ ID NO 35
<211> LENGTH: 447
<212> TYPE: PRT
<213> ORGANISM: Artificial Sequence
<220> FEATURE:
<223> OTHER INFORMATION: chimeric antibody heavy chain

<400> SEQUENCE: 35

Gln  Val  Gln  Leu  Gln  Gln  Ser  Gly  Pro  Glu  Leu  Val  Lys  Pro  Gly  Ala
1                 5                   10                  15

Ser  Val  Lys  Met  Ser  Cys  Lys  Ala  Ser  Gly  Tyr  Thr  Phe  Thr  Asp  Tyr
              20                  25                  30

Val  Ile  Ser  Trp  Val  Lys  Gln  Arg  Thr  Gly  Gln  Gly  Leu  Glu  Trp  Ile
          35                  40                  45

Gly  Glu  Ile  Tyr  Pro  Gly  Ser  Gly  Ser  Ile  Tyr  Tyr  Asn  Glu  Lys  Phe
     50                  55                  60

Lys  Gly  Lys  Ala  Thr  Leu  Thr  Ala  Asp  Thr  Ser  Ser  Asn  Thr  Ala  Tyr
65                  70                  75                  80

Met  Gln  Leu  Ser  Ser  Leu  Thr  Phe  Glu  Asp  Ser  Ala  Val  Ile  Phe  Cys
                 85                  90                  95

Ala  Arg  Gly  His  Tyr  Tyr  Gly  Tyr  Phe  Asp  Tyr  Trp  Gly  Gln  Gly  Thr
             100                 105                 110

Thr  Leu  Thr  Val  Ser  Ser  Ala  Ser  Thr  Lys  Gly  Pro  Ser  Val  Phe  Pro
         115                 120                 125

Leu  Ala  Pro  Ser  Ser  Lys  Ser  Thr  Ser  Gly  Gly  Thr  Ala  Ala  Leu  Gly
     130                 135                 140

Cys  Leu  Val  Lys  Asp  Tyr  Phe  Pro  Glu  Pro  Val  Thr  Val  Ser  Trp  Asn
145                 150                 155                 160

Ser  Gly  Ala  Leu  Thr  Ser  Gly  Val  His  Thr  Phe  Pro  Ala  Val  Leu  Gln
                 165                 170                 175

Ser  Ser  Gly  Leu  Tyr  Ser  Leu  Ser  Val  Val  Thr  Val  Pro  Ser  Ser
             180                 185                 190

Ser  Leu  Gly  Thr  Gln  Thr  Tyr  Ile  Cys  Asn  Val  Asn  His  Lys  Pro  Ser
         195                 200                 205

Asn  Thr  Lys  Val  Asp  Lys  Arg  Val  Glu  Pro  Lys  Ser  Cys  Asp  Lys  Thr
```

```
                210                 215                 220
His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly
            435                 440                 445

<210> SEQ ID NO 36
<211> LENGTH: 214
<212> TYPE: PRT
<213> ORGANISM: Artificial Sequence
<220> FEATURE:
<223> OTHER INFORMATION: chimeric antibody light chain

<400> SEQUENCE: 36

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Thr Ile Thr
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Thr Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
            130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 37
<211> LENGTH: 447
<212> TYPE: PRT
<213> ORGANISM: Artificial Sequence
<220> FEATURE:
<223> OTHER INFORMATION: chimeric antibody heavy chain
<220> FEATURE:
<221> NAME/KEY: VARIANT
<222> LOCATION: (298)..(298)
<223> OTHER INFORMATION: N298Q mutant not glycosylated

<400> SEQUENCE: 37

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Ile Tyr Tyr Asn Glu Lys Phe
    50                  55                  60

Lys Gly Lys Ala Thr Leu Thr Ala Asp Thr Ser Ser Asn Thr Ala Tyr
65                  70                  75                  80

Met Gln Leu Ser Ser Leu Thr Phe Glu Asp Ser Ala Val Ile Phe Cys
                85                  90                  95

Ala Arg Gly His Tyr Tyr Gly Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255
```

```
Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Gln Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 38
<211> LENGTH: 447
<212> TYPE: PRT
<213> ORGANISM: Artificial Sequence
<220> FEATURE:
<223> OTHER INFORMATION: chimeric antibody heavy chain
<220> FEATURE:
<221> NAME/KEY: VARIANT
<222> LOCATION: (254)..(254)
<223> OTHER INFORMATION: I254A mutant does not bind FcRn

<400> SEQUENCE: 38

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Ile Tyr Tyr Asn Glu Lys Phe
    50                  55                  60

Lys Gly Lys Ala Thr Leu Thr Ala Asp Thr Ser Asn Thr Ala Tyr
65                  70                  75                  80

Met Gln Leu Ser Ser Leu Thr Phe Glu Asp Ser Ala Val Ile Phe Cys
                85                  90                  95

Ala Arg Gly His Tyr Tyr Gly Tyr Phe Asp Tyr Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160
```

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ala Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 39
<211> LENGTH: 447
<212> TYPE: PRT
<213> ORGANISM: Artificial Sequence
<220> FEATURE:
<223> OTHER INFORMATION: chimeric antibody heavy chain
<220> FEATURE:
<221> NAME/KEY: VARIANT
<222> LOCATION: (254)..(254)
<223> OTHER INFORMATION: I254A mutant does not bind FcRn
<220> FEATURE:
<221> NAME/KEY: VARIANT
<222> LOCATION: (298)..(298)
<223> OTHER INFORMATION: N298Q mutant not glycosylated

<400> SEQUENCE: 39

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30
```

-continued

```
Val Ile Ser Trp Val Lys Gln Arg Thr Gly Gln Gly Leu Glu Trp Ile
         35                  40                  45
Gly Glu Ile Tyr Pro Gly Ser Gly Ser Ile Tyr Tyr Asn Glu Lys Phe
 50                  55                  60
Lys Gly Lys Ala Thr Leu Thr Ala Asp Thr Ser Ser Asn Thr Ala Tyr
 65                  70                  75                  80
Met Gln Leu Ser Ser Leu Thr Phe Glu Asp Ser Ala Val Ile Phe Cys
                 85                  90                  95
Ala Arg Gly His Tyr Tyr Gly Tyr Phe Asp Tyr Trp Gly Gln Gly Thr
                100                 105                 110
Thr Leu Thr Val Ser Ser Ala Ser Thr Lys Gly Pro Ser Val Phe Pro
                115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Arg Val Glu Pro Lys Ser Cys Asp Lys Thr
                210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ala Ser Arg
                245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
                275                 280                 285
Lys Thr Lys Pro Arg Glu Glu Gln Tyr Gln Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Arg Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly
                435                 440                 445
```